(12) United States Patent
Fukiage et al.

(10) Patent No.: US 6,551,999 B1
(45) Date of Patent: Apr. 22, 2003

(54) ANGIOGENESIS INHIBITOR

(75) Inventors: Chiho Fukiage, Katano (JP); Mitsuyoshi Azuma, Nishinomiya (JP); Jun Inoue, Kobe (JP); Masayuki Nakamura, Himeji (JP); Yuka Yoshida, Nishiwaki (JP)

(73) Assignee: Senju Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 09/243,822

(22) Filed: Feb. 3, 1999

Related U.S. Application Data

(62) Division of application No. 08/740,069, filed on Oct. 24, 1996, now Pat. No. 6,057,290.

(30) Foreign Application Priority Data

Oct. 25, 1995 (JP) .............................. 7-277485
Sep. 19, 1996 (JP) .............................. 8-248046

(51) Int. Cl.$^7$ ................................. C07K 5/06
(52) U.S. Cl. ........................... 514/19; 562/575
(58) Field of Search ................... 514/19, 345

(56) References Cited

U.S. PATENT DOCUMENTS

| | | | |
|---|---|---|---|
| 4,401,594 A | 8/1983 | Umezawa et al. | 260/112.5 |
| 5,081,284 A | 1/1992 | Higuchi et al. | 560/159 |
| 5,498,728 A | 3/1996 | Sohda et al. | 548/493 |
| 5,506,243 A * | 4/1996 | Ando et al. | 514/345 |
| 5,510,531 A | 4/1996 | Higuchi et al. | 564/159 |
| 5,607,831 A | 3/1997 | Henkart et al. | 435/5 |
| 5,639,781 A | 6/1997 | Sohda et al. | 514/419 |
| 5,658,885 A | 8/1997 | Lee et al. | 514/119 |

FOREIGN PATENT DOCUMENTS

| | | |
|---|---|---|
| EP | 0 236 163 A1 | 9/1987 |
| EP | 0 395 309 A1 | 10/1990 |
| EP | 0 504 938 | 9/1992 |
| EP | 0 520 336 A2 | 12/1992 |
| EP | 0 731 107 A1 | 9/1996 |
| EP | 0 838 460 A1 | 4/1998 |
| JP | 50-137951 | 11/1975 |
| WO | 92/14696 | 9/1992 |
| WO | 96/10014 | 4/1996 |
| WO | 96/14857 | 5/1996 |
| WO | 96/35711 | 11/1996 |
| WO | 97/21690 | 6/1997 |

OTHER PUBLICATIONS

P. Bagavandoss et al., "Recombinant Truncated Thrombospondin–1 Monomer Modulates Endothelial Cell Plasminogen Activator Inhibitor 1 Accumulation and Proliferation In vitro", Biochemical and Biophysical Research Communications, vol. 92, No. 2, pp. 325–332, 1993.
Patent Abstracts of Japan, vol. 013, No. 101, Mar. 9, 1989 & JP 63 275576 A, Nov. 14, 1988 *abstract*.
Patent Abstracts of Japan, vol. 013, No. 101, Mar. 9, 1989 & JP 63 275575, Nov. 14, 1988, *abstract*.
Maki et al., J. Biol. Chem., vol. 264, No. 32, Nov. 15, 1989, pp. 18866–18869.
Eto et al., J. Biol. Chem., vol. 270, No. 42, Oct. 20, 1995, pp. 25115–25120.

* cited by examiner

Primary Examiner—Christopher S. F. Low
Assistant Examiner—David Lukton
(74) Attorney, Agent, or Firm—Wenderoth, Lind & Ponack, L.L.P.

(57) ABSTRACT

An angiogenesis inhibitor comprising a cysteine protease inhibitory compound. As the preferable cysteine protease inhibitory compound, epoxysuccinic acid compounds, peptide halohydrazide compounds, calpain inhibitory compounds, compounds of the formula (I)

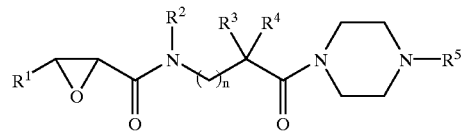

and compounds of the formula (VI)

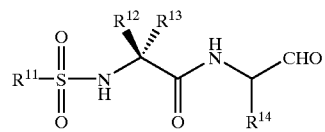

can be used. The angiogenesis inhibitor of the present invention suppresses new formation of blood vessels in the living tissues, so that it can be used as a superior therapeutic or prophylactic agent of angiogenesis associated with wound healing, inflammation, growth of tumor and the like; and angiogenesis as seen in diabetic retinopathy, prematurity retinopathy, retinal venous occlusion, senile discoid macular degeneration and the like, as well as for prevention of metastasis of tumors.

1 Claim, 5 Drawing Sheets bFGF-containing pellet 27 mer calpastatin peptide (0.03 μmole)-containing pellet
+ bFGF-containing pellet 27 mer calpastatin peptide (0.1 μmole)-containing pellet
+ bFGF-containing pellet bFGF-containing pellet leupeptin (0.1 μmole)-containing pellet
+ bFGF-containing pellet

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Gly Lys Arg Glu Val Thr Ile Pro Pro Lys Tyr Arg
1               5                   10

(2) INFORMATION FOR SEQ ID NO:2:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Gly Lys Arg Glu Val Thr Leu Pro Pro Lys Tyr Arg
1               5                   10

```
(2) INFORMATION FOR SEQ ID NO:3:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Gly Glu Asp Asp Glu Thr Ile Pro Ser Glu Tyr Arg
 1               5                  10

(2) INFORMATION FOR SEQ ID NO:4:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Gly Glu Asp Asp Glu Thr Val Pro Pro Glu Tyr Arg
 1               5                  10

(2) INFORMATION FOR SEQ ID NO:5:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Gly Glu Asp Asp Glu Thr Val Pro Ala Glu Tyr Arg
 1               5                  10

(2) INFORMATION FOR SEQ ID NO:6:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Gly Glu Lys Glu Glu Thr Ile Pro Pro Asp Tyr Arg
 1               5                  10

(2) INFORMATION FOR SEQ ID NO:7:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Gly Glu Arg Asp Asp Thr Ile Pro Pro Glu Tyr Arg
 1               5                  10
```

-continued (2) INFORMATION FOR SEQ ID NO:8:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Asp Pro Met Ser Ser Thr Tyr Ile Glu Glu Leu Gly Lys Arg Glu
 1               5                  10                  15

Val Thr Ile Pro Pro Lys Tyr Arg Glu Leu Leu Ala
                20                  25
```

ANGIOGENESIS INHIBITOR

This application is a divisional of Ser. No. 08/740,069 filed Oct. 24, 1996 now U.S. Pat. No. 6,057,290.

TECHNICAL FIELD

The present invention relates to an angiogenesis inhibitor comprising a cysteine protease inhibitory compound.

BACKGROUND OF THE INVENTION

An angiogenesis is a phenomenon wherein new blood vessels are created to form a new vascular network in the living body. The angiogenesis is found under normal physiological environment such as genesis and reproduction with regard to embryo, fetus, placenta, uterus and the like. It is also a pathologic phenomenon which accompanies wound healing, inflammation, growth of tumor and the like, and which is ophthalmologically seen in diabetic retinopathy, prematurity retinopathy, retinal venous occlusion, senile discoid macular degeneration and the like.

The angiogenesis greatly varies depending on the function and growth of endothelial cells, and is considered to be a cascade reaction which proceeds in the smallest vein along the following steps. That is, new blood vessels are presumably formed as a result of consecutive elementary reactions of (1) activation of vascular endothelial cells which are in the stage of rest upon differentiation, (2) destruction of cell matrix such as basement membrane by endothelial cells which expressed protease activity, (3) migration of endothelial cells, (4) proliferation of endothelial cells and (5) tube-formation by differentiation of endothelial cells [T. Oikawa, Drug News Perspest, Vol. 6, pp. 157–162 (1993)]. Each step of these reactions has been clarified to be promoted by angiogenesis promoters. Such angiogenesis promoters include, for example, blood vessel inducing factors [e.g., tumor angiogenetic factor (TAF)] secreted from tumor tissues, and growth factors such as fibroblast growth factor (FGF) present in various normal tissues, endothelial cell growth facor derived from platelets and vascular endothelial cell growth factor. In addition, cytokine, prostaglandine, monobutylin and angiogenine reportedly have similar direct or indirect effects [M. Klagsbrun et al., Annu. Rev. Physiol., Vol. 53, pp. 217–239 (1991)].

A substance which suppresses such angiogenesis include angiostatic steroids [Folkman, J. et al., Science, Vol. 221, p. 719 (1983)] such as cortisone which inhibits growth of endothelial cells; medroxyproge-sterone acetate which inhibits production of plasminogen activator by endothelial cells; fumagillin acid derivatives which inhibit proliferation of endothelial cells and tube-formation; polysaccharide sulfate SD-4152 which inhibits proliferation and migration of endothelial cells; and retinoic acid which is responsible for modification of endothelial cell differentiation [Tsutomu Oikawa, *Kekkan to Naihi*, vol. 2, pp. 470–480 (1992)].

However, the above-mentioned drugs which inhibit angiogenesis have not been complete therapeutic agents for clinically suppressing angiogenesis, since some of them cause strong side-effects, thereby posing problems in terms of safety, and others only show insufficient effects.

SUMMARY OF THE INVENTION

It is therefore an object of the present invention to provide a pharmaceutical agent which provides strong angiogenesis-inhibitory effects.

According to the present invention, there has been provided (1) an angiogenesis inhibitor comprising a cysteine protease inhibitory compound.

Cysteine protease is a protease having a cysteine residue in the active site of the enzyme molecule and includes such species as cathepsin B, H, and L and dipeptidyl peptidase, all of which are lysosomal enzyme fractions, and calpain which occurs in the cytoplasm, among others. Though much remains to be explored about the physiological roles of these enzymes, a considerable amount of light has been cast on their roles in recent years. For example, calpain is known to be a protease ubiquitous in life, which is activated by calcium ions and has the optimum pH in neutral. As elucidated to this day, it takes part in degradation of the skeletal protein of cells, activation of inert cell precursors such as protein kinase C, and degradation of receptor proteins. It has also been shown that the abnormality of this enzyme activity is involved in many diseases. For example, its involvement in refractory diseases such as cerebral apoplexy (stroke), subarachnoid hemorrhage, Alzheimer's disease, ischemic diseases, muscular dystrophy, cataract, platelet aggregation disorder, arthritis, and osteoporosis, among other diseases. [Trends in Pharmacological Science, Vol. 15, p. 412 (1994)].

The angiogenesis inhibitor of the present invention may have the following modes.

(2) The angiogenesis inhibitor of above (1) wherein the cysteine protease inhibitory compound is a calpain inhibitory compound.

(3) The angiogenesis inhibitor of above (2) wherein the calpain inhibitory compound is at least one compound selected from calpastatin and calpastatin peptide.

(4) The angiogenesis inhibitor of above (3) wherein the calpastatin peptide is at least one compound selected from peptides having an amino acid sequence of the following formula:

-Gly-A-Tyr-Argwherein A is -Lys-Arg-Glu-Val-Thr-Ile-Pro-Pro-Lys- (SEQ ID NO.1), -Lys-Arg-Glu-Val-Thr-Leu-Pro-Pro-Lys- (SEQ ID NO.2), -Glu-Asp-Asp-Glu-Thr-Ile-Pro-Ser-Glu- (SEQ ID NO.3), -Glu-Asp-Asp-Glu-Thr-Val-Pro-Pro-Glu- (SEQ ID NO.4), -Glu-Asp-Asp-Glu-Thr-Val-Pro-Ala-Glu- (SEQ ID NO.5), -Glu-Lys-Glu-Glu-Thr-Ile-Pro-Pro-Asp- (SEQ ID NO.6) or -Glu-Arg-Asp-Asp-Thr-Ile-Pro-Pro-Glu- (SEQ ID NO.7).

(5) The angiogenesis inhibitor of above (4) wherein the calpastatin peptide has an amino acid sequence of the following formula:

Asp-Pro-Met-Ser-Ser-Thr-Tyr-Ile-Glu-Glu-Leu-Gly-Lys-Arg-Glu-Val-Thr-Ile-Pro-Pro-Lys-Tyr-Arg-Glu-Leu-Leu-Ala. (SEQ ID NO.8).

(6) The angiogenesis inhibitor of above (2) wherein the calpain inhibitory compound inhibits $Ca^{2+}$-binding site having a high homology with calmodulin in calpain.

(7) The angiogenesis inhibitor of above (6) wherein the compound which inhibits $Ca^{2+}$-binding site having a high homology with calmodulin is at least one compound selected from calmodulin antagonistic compounds.

(8) The angiogenesis inhibitor of above (1) wherein the cysteine protease inhibitory compound is at least one compound selected from the group consisting of epoxysuccinic peptide compounds, peptide aldehyde compounds, peptide halomethane compounds, peptide diazomethane compounds, peptide halohydrazide compounds, peptide disulfide compounds, peptide ketoamide compounds and isocoumarine compounds.

(9) The angiogenesis inhibitor of above (8) wherein the cysteine protease inhibitory compound is an epoxysuccinic peptide compound.

(10) The angiogenesis inhibitor of above (9) wherein the cysteine protease inhibitory compound is an epoxysuccinic peptide compound of the formula (I):

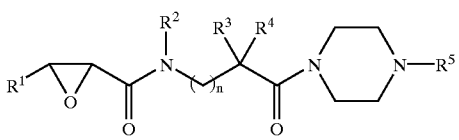

(I)

wherein $R^1$ is an optionally esterified carboxy or an optionally substituted carboxamide;

$R^2$ is a hydrogen or a lower (unless otherwise specified, "lower" means "having 1 to 6 carbon atoms" in the present specification) alkyl or forms a ring together with $R^3$ or $R^4$;

$R^3$ and $R^4$ are the same or different and each is a hydrogen, an optionally substituted lower alkyl, an optionally substituted sulfide, or $R^3$ and $R^4$ combindly form a ring;

$R^5$ is a substituted phenyl of the formula (II)

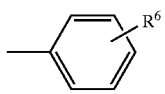

(II)

wherein $R^6$ is halogen atom or alkoxy, or a substituted sulfonyl of the formula (III)

(III)

wherein $R^7$ is aryl optionally substituted by lower alkyl or optionally substituted amino; and n is 0 or 1, or a salt thereof.

(11) The angiogenesis inhibitor of above (10) wherein $R^1$ is an optionally esterified carboxy, or carboxamide optionally substituted by hydroxy or aralkyloxy.

(12) The angiogenesis inhibitor of above (10) wherein $R^2$ is hydrogen or methyl.

(13) The angiogenesis inhibitor of above (10) wherein $R^2$ and $R^3$, or $R^2$ and $R^4$ combinedly form a pyrrolidine ring.

(14) The angiogenesis inhibitor of above (10) wherein $R^3$ and $R^4$ are the same or different and each is hydrogen, lower alkyl optionally substituted by aromatic group or carbamoyl, or sulfide optionally substituted by acylamino.

(15) The angiogenesis inhibitor of above (10) wherein $R^3$ and $R^4$ combinedly form a cyclopentane ring.

(16) The angiogenesis inhibitor of above (10) wherein $R^6$ of the formula (II) is chlorine or fluorine.

(17) The angiogenesis inhibitor of above (10) wherein $R^7$ of the formula (III) is phenyl or dimethylamino optionally substituted by lower alkyl.

(18) The angiogenesis inhibitor of above (8) wherein the cysteine protease inhibitory compound is a peptide aldehyde compound.

(19) The angiogenesis inhibitor of above (18) wherein the peptide aldehyde compound is leupeptin.

(20) The angiogenesis inhibitor of above (18) wherein the peptide aldehyde compound is a compound of the formula (VI):

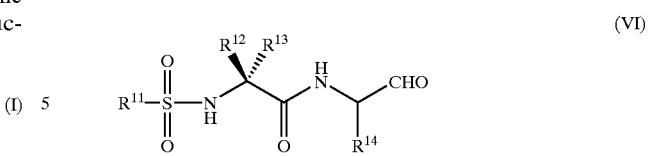

(VI)

wherein $R^{11}$ is an optionally substituted aryl having 6 to 10 carbon atoms; $R^{12}$ and $R^{13}$ are the same or different and each is a hydrogen, a $C_1$–$C_4$ is alkyl, or $R^{12}$ and $R^{13}$ combinedly form a ring having 3 to 7 carbon atoms; and $R^{14}$ is a lower alkyl optionally substituted by aryl, cycloalkyl or aromatic heterocycle, or a salt thereof.

(21) The angiogenesis inhibitor of above (20) wherein $R^{11}$ is phenyl or naphthyl optionally substituted by fluorine, chlorine or methyl.

(22) The angiogenesis inhibitor of above (21) wherein $R^{11}$ is a member selected from 4-fluorophenyl, 4-chlorophenyl, p-tolyl and 2-naphthyl.

(23) The angiogenesis inhibitor of above (20) wherein $R^{12}$ is propyl, isopropyl or tert-butyl, and $R^{13}$ is hydrogen.

(24) The angiogenesis inhibitor of above (23) wherein $R^{12}$ is isopropyl and $R^{13}$ is hydrogen.

(25) The angiogenesis inhibitor of above (20) wherein $R^{12}$ and $R^{13}$ combinedly form cyclohexylidene.

(26) The angiogenesis inhibitor of above (20) wherein $R^{14}$ is isobutyl, benzyl, cyclohexylmethyl or indol-3-ylmethyl.

DISCLOSURE OF THE INVENTION

Figure 1:
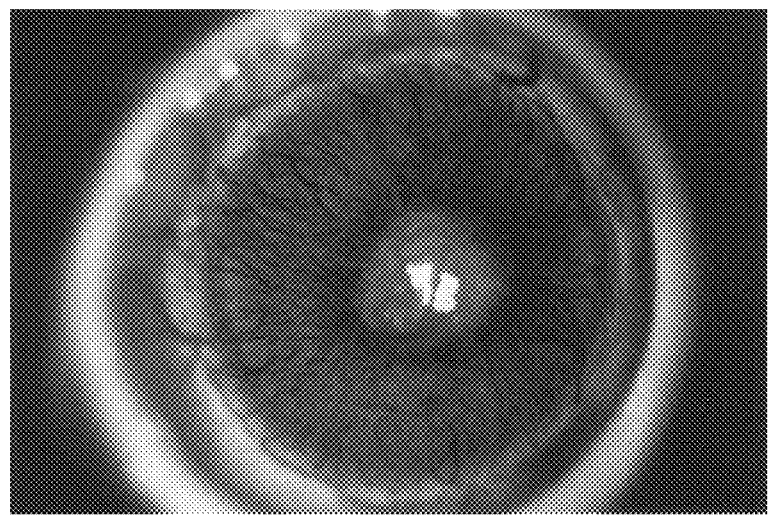
FIG. 1(A), FIG. 1(B) and FIG. 1(C) show cornea of guinea pig observed with a slit lamp, at 9 days after implantation of bFGF-containing pellet, and 27 mer calpastatin peptide (0.03 μmole and 0.1 μmole)-containing pellet together with bFGF-containing pellet.
Figure 1:
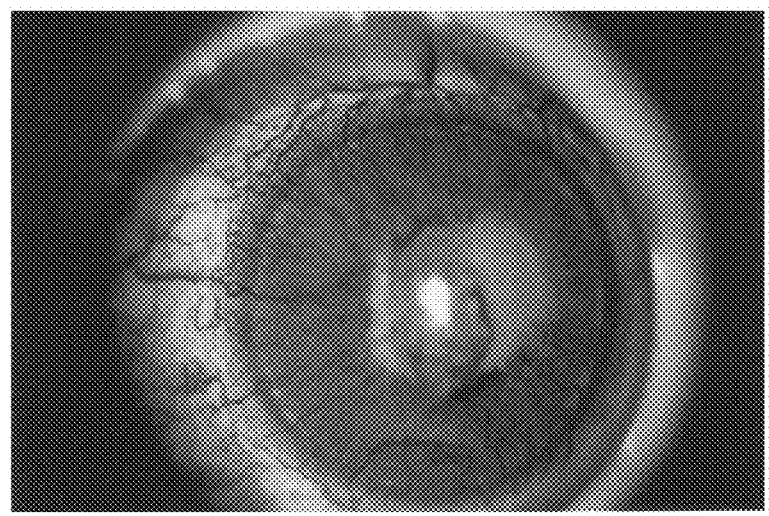
Figure 1:
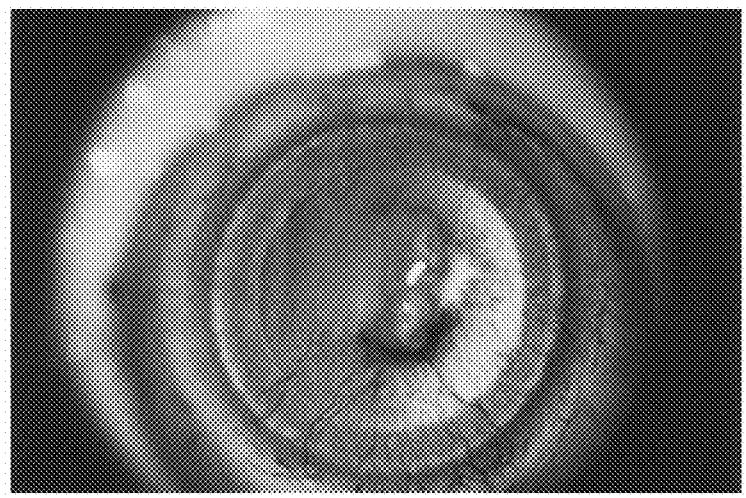

The cysteine protease inhibitor to be used for the angiogenesis inhibitor of the present invention may be any compound as long as it can inhibit cysteine protease. Examples of such compound include epoxysuccinic peptide compounds such as (+)-(2S,3S)-3-[[[1-[[[4-[(aminoiminomethyl)amino]butyl]amino]carbonyl]-3-methylbutyl]amino]-carbonyl]-2-oxyranecarboxylic acid (E-64), (+)-(2S,3S)-3-[(S)-3-methyl-1-(3-methylbutylcarbamoyl)butylcarbamoyl]-2-oxyranecarboxylic acid (E-64c) and ethyl (+)-(2S,3S)-3-[(S)-3-methyl-1-(3-methylbutylcarbamoyl)butylcarbamoyl]-2-oxyranecarboxylate (E-64d); peptide aldehyde compounds such as leupeptin, calpeptin, Ac-Leu-Leu-nLeu-H (calpain inhibitor peptide I), Ac-Leu-Leu-nMet-H (calpain inhibitor peptide II), Z-Val-Phe-H (MDL28170) and Boc-Leu-Nle-H; peptide halomethane compounds such as Z-Leu-Leu-Tyr-CH$_2$F; peptide diazomethane compounds such as Z-Leu-Leu-Tyr-CHN$_2$; peptide halohydrazide compounds such as Z-3-I-Tyr-NHNHCOCH$_2$I; peptide disulfide compounds such as Leu-Leu-(3-nitro-2-pyridinesulfinyl)Cys-NH$_2$; peptide ketoamide compounds such as Z-Leu-Abu-CONHEt (AK275); and isocoumarine compounds such as 7-amino-4-chloro-3-(3-isothioureidopropoxy)isocoumarine.

The cysteine protease inhibitory compound to be used for the angiogenesis inhibitor of the present invention may be a substance which specifically inhibits calpain or cathepsin B, H and L, from among cysteine proteases. Examples of the substance which specifically inhibits calpain include calpastatin, calpastatin peptide and the like.

The above-mentioned calpastatin peptide is preferably a peptide having an amino acid sequence of the following formula:

-Gly-A-Tyr-Argwherein A is -Lys-Arg-Glu-Val-Thr-Ile-Pro-Pro-Lys-, -Lys-Arg-Glu-Val-Thr-Leu-Pro-Pro-Lys-, -Glu-Asp-Asp-Glu-Thr-Ile-Pro-Ser-Glu-, -Glu-Asp-Asp-Glu-Thr-Val-Pro-Pro-Glu-, -Glu-Asp-Asp-Glu-Thr-Val-Pro-Ala-Glu-, -Glu-Lys-Glu-Glu-Thr-Ile-Pro-Pro-Asp- or -Glu-Arg-Asp-Asp-Thr-Ile-Pro-Pro-Glu-, particularly, a peptide (27 mer calpastatin peptide) having an amino acid sequence of the following formula:

Asp-Pro-Met-Ser-Ser-Thr-Tyr-Ile-Glu-Glu-Leu-Gly-Lys-Arg-Glu-Val-Thr-Ile-Pro-Pro-Lys-Tyr-Arg-Glu-Leu-Leu-Ala.

The cysteine protease inhibitory compound to be used for the angiogenesis inhibitor of the present invention may contain a substance which inhibits Ca$^{2+}$-binding site having a high homology with calmodulin. Examples of such substance include calmodulin antagonistic compounds such as melittin, calmidazolium, trifluoroperazine and N-(6-aminohexyl)-5-chloro-1-naphthalenesulfonamide hydrochloride (W7), and ethylenediaminetetraacetic acid (EDTA).

These cysteine protease inhibitory compounds may be used alone or in combination.

As an epoxysuccinine peptide compound having strong cysteine protease inhibitory effect, a new compound of the following formula may be used.

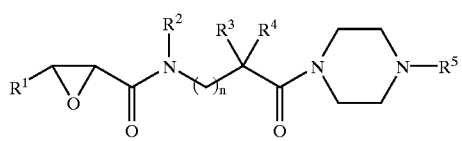

wherein each symbol is as defined above.

Referring to the above formula (I), the optionally esterified carboxy represented by R$^1$ includes but is not limited to carboxy and alkoxycarboxy. The alkoxy moiety of said alkoxycarboxy may be C$_1$–C$_6$ alkoxy and preferably C$_1$–C$_4$ alkoxy, such as methoxy, ethoxy, propoxy, isopropoxy, butoxy, isobutoxy, sec-butoxy, and tert-butoxy. Particularly preferred is ethoxy.

The substituent for said optionally substituted carboxamide represented by R$^1$ includes hydroxy, alkoxy (methoxy, ethoxy, propoxy, etc.), and aralkyloxy (benzyloxy etc.). Preferred are hydroxy and benzyloxy.

The lower alkyl for R$^2$ includes C$_1$–C$_6$ linear- or branched alkyl or preferably C$_1$–C$_4$ alkyl, such as methyl, ethyl, n-propyl, isopropyl, n-butyl, isobutyl, sec-butyl, tert-butyl, n-pentyl, isopentyl, neopentyl, tert-pentyl, n-hexyl, isohexyl, 4-methylpentyl, 1,1-dimethylbutyl, 2,2-dimethylbutyl, 3,3-dimethylbutyl, and 2-ethylbutyl. Preferred are hydrogen and methyl.

The ring that may be formed combinedly by R$^2$ and either R$^3$ or R$^4$ includes but is not limited to aziridine, azetidine, pyrrolidine, and piperidine. Particularly preferred is pyrrolidine.

The alkyl of said optionally substituted lower alkyl for R$^3$ and R$^4$ includes C$_1$–C$_6$ linear or branched alkyl such as methyl, ethyl, n-propyl, isopropyl, n-butyl, isobutyl, sec-butyl, tert-butyl, n-pentyl, isopentyl, neopentyl, tert-pentyl, n-hexyl, 4-methylpentyl, 1,1-dimethylbutyl, 2,2-dimethylbutyl, 3,3-dimethylbutyl, and 2-ethylbutyl. Preferred are methyl, ethyl, isobutyl, and sec-butyl. The substituent optionally present on said alkyl includes an aromatic ring and carbamoyl. The aromatic ring includes aromatic carbocycles such as benzene ring and aromatic heterocycles such as indole ring. Particularly preferred is benzene ring.

The sulfide group of said optionally substituted sulfide for R$^3$ and R$^4$ includes alkylthioalkyl and preferably C$_1$–C$_4$ alkyl-thio-C$_1$–C$_4$ alkyl, such as dimethyl sulfide, diethyl sulfide, dipropyl sulfide, dibutyl sulfide, dipentyl sulfide, dihexyl sulfide, methylethyl sulfide, methylpropyl sulfide, and ethylbutyl sulfide. Preferred are dimethyl sulfide and methylethyl sulfide. The substituent optionally present on said sulfide includes acylamino. The acylamino includes but is not limited to formylamino, acetylamino, propionylamino, butyrylamino, isobutyrylamino, valerylamino, isovalerylamino, pivaloylamino, and n-hexanoylamino. Preferred is acetylamino.

The ring optionally formed combinedly by R$^3$ and R$^4$ includes cyclopropane, cyclobutane, cyclopentane, cyclohexane, cycloheptane, etc. Particularly preferred is cyclopentane.

Referring to the substituent R$^6$ for said substituted phenyl of formula (II), the halogen includes but is not limited to fluorine, chlorine, bromine, and iodine. Preferred are fluorine and chlorine. The halogen may be bonded at any of meta, para, and ortho positions.

Referring further to the substituent R$^6$ for said substituted phenyl of formula (II), the alkoxy includes C$_1$–C$_6$ alkoxy and preferably C$_1$–C$_4$ alkoxy, such as methoxy, ethoxy, propoxy, isopropoxy, butoxy, isobutoxy, sec-butoxy, and tert-butoxy. Particularly preferred is methoxy.

Referring to the substituent R$^7$ for the substituted sulfonyl of formula (III), the aryl of said aryl optionally substituted by lower alkyl includes but is not limited to phenyl and naphthyl. The lower alkyl optionally substituting said aryl includes methyl, ethyl, propyl, isopropyl, butyl, etc. and may be bonded at any position of the aryl group.

Referring further to the substituent R$^7$ for said substituted sulfonyl of formula (III), the amino includes amino and amino substituted by one or two C$_1$–C$_6$ linear, branched or cyclic alkyl, such as methylamino, dimethylamino, ethylamino, diethylamino, propylamino, dipropylamino, isopropylamino, diisopropylamino, butylamino, dibutylamino and cyclohexylamino. Particularly preferred is dimethylamino.

In the context of the present invention, the salt of the compound of formula (I) is preferably a physiologically acceptable salt, thus including salts with inorganic bases, salts with organic bases, salts with inorganic acids, salts with organic acids, and salts with basic or acidic amino acids. The preferred inorganic base salt includes alkali metal salts such as sodium salt and potassium salt, alkaline earth metal salts such as calcium salt and magnesium salt, aluminum salt, and ammonium salt. The preferred organic base salt includes salts with trimethylamine, pyridine, picoline, ethanolamine, diethanolamine, triethanolamine, dicyclohexylamine, and N,N-dibenzylethylenediamine. The preferred inorganic acid salt includes salts with hydrochloric acid, hydrobromic acid, nitric acid, sulfuric acid, and phosphoric acid. The preferred organic acid salt includes salts with formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluene sulfonic acid. The preferred salt with a basic amino acid includes salts with arginine, lysine, ornithine, etc., while the preferred salt with an acidic amino acid includes salts with aspartic acid and glutamic acid.

The compound of general formula (I) according to the present invention can be produced in accordance with the following reaction scheme.

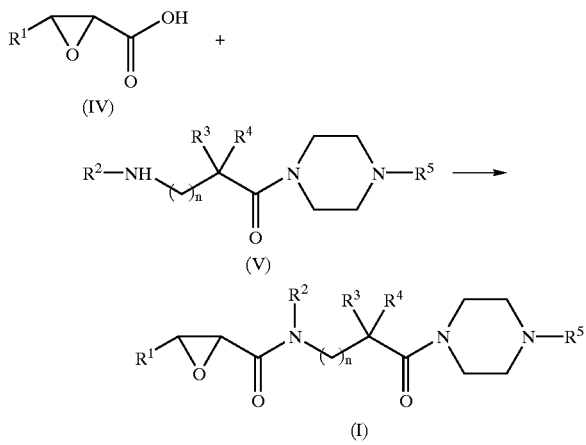

wherein each symbol is as defined above. In this process, a compound of the formula (IV) [hereinafter sometimes referred to as compound (IV)] or a reactive derivative in the carboxyl thereof, or a salt thereof, is reacted with a compound of the formula (V) [hereinafter sometimes referred to as compound (V)] or a reactive derivative thereof, or a salt thereof, to provide compound (I).

The above reaction can be carried out by the routine liquid-phase or solid-phase (stationary) technique known to those skilled in peptide synthesis. As to such known routine procedures and analogous procedures, the descriptions in the following literature are incorporated herein by reference: Izumiya, Nobuo et al.: *Pepuchido Gosei no Kiso to Jikken* (Fundamentals and Experiments in Peptide Synthesis), Maruzen, 1985; Yajima, Haruaki & Sakakibara, Shumpei: *Seikagaku Jikken Koza* 1 (Biochemical Experiment Series 1), Japanese Biochemical Society (ed.), Tokyo Kagaku Dojin, 1977; Kimura, Toshiya: *Zoku Seikagaku Jikken Koza* 1 (New Biochemical Experiment Series 1, Japanese Biochemical Society (ed.), Tokyo Kgaku Dojin, 1987; Suzuki, Nobuo: *Jikken Kogaku Koza* (4th Edition) 22, Yuki Gosei IV (Experimental Chemistry Series (Edition IV) 22, Organic Synthesis IV), The Chemical Society of Japan (ed.), Maruzen, 1992.

The preferred reactive derivative in the carboxyl of compound (IV) includes acid halide, acid anhydride, activated amide, and activated ester. The acid halide includes but is not limited to acid chloride. The acid anhydride includes mixed acid anhydrides with various acids such as substituted phosphoric acid (dialkylphosphoric acid, phenylphosphoric acid, diphenylphosphoric acid, dibenzyl phosphoric acid, halophosphoric acid, etc.), dialkylphosphorous acid, sulfurous acid, thiosulfuric acid, sulfuric acid, sulfonic acids (methanesulfonic acid, etc.), aliphatic carboxylic acids (acetic acid, propionic acid, butyric acid, isobutyric acid, pivalic acid, pentanoic acid, isopentanoic acid, trichloroacetic acid, etc.), and aromatic carboxylic acids (benzoic acid etc.) as well as symmetric acid anhydride. The preferred activated amide includes but is not limited to imidazole, 4-substituted imidazole, dimethylpyrazole, triazole, and tetrazole. The preferred activated ester includes but is not limited to the cyanomethyl ester, methoxymethyl ester, dimethyliminomethyl ester, vinyl ester, propargyl ester, p-nitrophenyl ester, trichlorophenyl ester, pentachlorophenyl ester, methylphenyl ester, phenylazophenyl ester, phenylthio ester, p-nitrophenylthio ester, p-cresylthio ester, carboxymethylthio ester, pyranyl ester, pyridyl ester, 8-quinolylthio ester, etc. and esters with N-hydroxy compounds such as N,N-dimethylhydroxyamine, 1-hydroxy-2-(1H)-pyridone, N-hydroxysuccinimide, N-hydroxyphthalimide, 1-hydroxy-1H-benzotriazole, etc. The preferred salt of compound (IV) or a reactive derivative thereof includes alkali metal salts, e.g. sodium salt, potassium salt, etc., alkaline earth metal salts such as calcium salt, magnesium salt, etc., aluminum salt, and ammonium salt, as well as salts with organic bases such as trimethylamine salt, triethylamine salt, pyridine salt, picoline salt, ethanolamine salt, diethanolamine salt, triethanolamine salt, dicyclohexylamine salt, N,N-dibenzylethylenediamine salt, etc. The kind of reactive derivative can be selected according to the type of compound (IV) to be used.

The preferred reactive derivative in the amino group of compound (V) includes Schiff base type imino and enamine tautomers available on reaction of compound (V) with carbonyl compounds such as aldehydes and ketones, silyl derivatives available on reaction of compound (V) with silyl compounds such as bis(trimethylsilyl)acetamide, mono (trimethylsilyl)acetamide, bis(trimethylsilyl)urea, etc., and derivatives available on reaction of compound (V) with phosphorus trichloride or phosgene. The preferred salts of the compound (V) and its reactive derivative include salts with inorganic acids, such as hydrochloride, hydrobromide, nitrate, sulfate, phosphate, etc. and salts with organic acids, such as formate, acetate, trifluoroacetate, fumarate, oxalate, tartrate, maleate, citrate, succinate, malate, methanesulfonate, benzenesulfonate, p-toluenesulfonate, etc. These reactive derivatives can be selectively used according to the type of compound (V).

The reaction between compounds (IV) and (V) is generally conducted in water, a common solvent, e.g. alcohol (e.g. methanol, ethanol, etc.), acetone, dioxane, acetonitrile, chloroform, methylene chloride, ethylene chloride, tetrahydrofuran, ethyl acetate, N,N-dimethylformamide, and pyridine, although the reaction can be carried out in any other organic solvent that does not interfere with the reaction. The common organic solvent mentioned above may be used in admixture with water. When compound (IV) is used either in a free form or in the form of a salt in the above reaction, the reaction is preferably conducted in the presence of a common condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'- carbonyl-bis(2-methylimidazole), penta-methyleneketene-N-cyclohexylimine, diphenylketene-N-cyclohexylimine, ethoxyacetylene, 1-alkoxy-1-chloroethylene, trimethyl phosphite, ethyl polyphosphate, isopropyl polyphosphate, phosphorus oxychloride, diphenylphosphorylazide, thionyl chloride, oxalyl chloride, haloformic acid lower alkyl esters (e.g. ethyl chloroformate, isopropyl chloroformate, etc.), triphenylphosphine, N-hydroxybenzotriazole, 1-(p-chlorobenzenesulfonyloxy)-6-chloro-1H-benzotriazole, Vilsmeier reagents prepared by reacting N,N-dimethylformamide with thionyl chloride, phosgene, trichloromethyl chloroformate, phosphorus oxychloride, or the like. The reaction may be carried out in the presence of an inorganic or organic base, e.g. alkali metal hydrogencarbonate, tri($C_1$–$C_6$)alkylamine, pyridine, N-($C_1$–$C_6$)alkylmorpholine, N,N-di-($C_1$–$C_6$)alkylbenzylamine, etc. The reaction temperature is not so critical and the reaction can be generally carried out under cooling, at ambient temperature, or under mild heating.

The structural formulas of the compounds synthesized in the Examples which appear hereinafter are shown below.

TABLE 1

| Com. No. | n | $R^1$ | $R^2$ | $R^3$ | $R^4$ | $R^6$ |
|---|---|---|---|---|---|---|
| 1 | 0 | —COOEt | H | benzyl | H | 4-fluoro |
| 2 | 0 | —COOEt | H | benzyl | H | 2-fluoro |
| 3 | 0 | —COOEt | H | isobutyl | H | 4-fluoro |
| 4 | 0 | —COOEt | H | isobutyl | H | H |
| 7 | 0 | —COOEt | H | isobutyl | H | 2-chloro |
| 8 | 0 | —COOEt | H | isobutyl | H | 3-chloro |
| 9 | 0 | —COOEt | H | isobutyl | H | 4-chloro |
| 10 | 0 | —COOEt | H | isobutyl | H | 4-methoxy |
| 11 | 0 | —COOH | H | benzyl | H | 4-fluoro |
| 12 | 0 | —COOH | H | benzyl | H | 2-fluoro |
| 13 | 0 | —COOH | H | isobutyl | H | 4-fluoro |
| 14 | 0 | —COOH | H | isobutyl | H | H |
| 17 | 0 | —COOH | H | isobutyl | H | 2-chloro |
| 18 | 0 | —COOH | H | isobutyl | H | 3-chloro |
| 19 | 0 | —COOH | H | isobutyl | H | 4-chloro |
| 20 | 0 | —COOH | H | isobutyl | H | 4-methoxy |
| 21 | 0 | —COOH | H | isopropyl | H | 2-chloro |
| 22 | 0 | —COOH | H | H | H | 2-chloro |
| 23 | 0 | —COOH | H | methyl | H | 2-chloro |
| 24 | 0 | —COOH | H | sec-butyl | H | 2-chloro |
| 25 | 1 | —COOH | H | H | H | 2-chloro |
| 26 | 0 | —COOH | methyl | H | H | 2-chloro |
| 27 | 0 | —COOH | | pyrrolidinyl | H | 2-chloro |
| 28 | 0 | —COOH | H | —$CH_2$—S—$CH_2NHCOCH_3$ | H | 2-chloro |
| 29 | 0 | —COOH | H | —$CH_2CH_2$—S—$CH_3$ | H | 2-chloro |
| 30 | 0 | —COOH | H | —$CH_2CH_2CONH_2$ | H | 2-chloro |
| 31 | 0 | —COOH | H | cyclopentyl | | 4-fluoro |

TABLE 2

| Com. No. | n | $R^1$ | $R^2$ | $R^3$ | $R^4$ | $R^7$ |
|---|---|---|---|---|---|---|
| 5 | 0 | —COOEt | H | isobutyl | H | —N(CH$_3$)$_2$ |
| 6 | 0 | —COOEt | H | isobutyl | H | 4-methylphenyl |
| 15 | 0 | —COOH | H | isobutyl | H | —N(CH$_3$)$_2$ |
| 16 | 0 | —COOH | H | isobutyl | H | 4-methylphenyl |

TABLE 2-continued structure: R¹-epoxide-C(O)-N(R²)-(C)ₙ-C(R³)(R⁴)-C(O)-N-piperazine-N-SO₂-R⁷

| Com. No. | n | R¹ | R² | R³ | R⁴ | R⁷ |
|---|---|---|---|---|---|---|
| 32 | 0 | —CONHOCH₂—phenyl | H | isobutyl | H | 4-methylphenyl (—C₆H₄—CH₃) |
| 33 | 0 | —CONHOH | H | isobutyl | H | 4-methylphenyl (—C₆H₄—CH₃) |

As a peptide aldehyde compound having a strong cysteine protease inhibitory effect, a new compound of the following formula (VI) may be used,

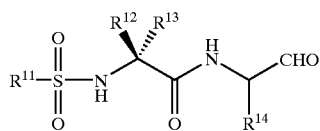

(VI)

wherein each symbol is as defined above.

Note that when the amino acid to be used in the present invention has an optical isomer, it is an L compound unless specifically indicated.

The $C_6$–$C_{10}$ aryl at $R^{11}$ may be, for example, phenyl, naphthyl, pentaphenyl, indenyl and azulenyl, with preference given to phenyl and naphthyl. The substituent optionally possessed by aryl may be, for example, halogen atom (e.g., fluorine and chlorine), alkyl having 1 to 5 carbon atoms, trifluoromethyl, alkoxy having 1 to 5 carbon atoms, hydroxy, acyloxy having 2 to 5 carbon atoms, carboxyl and acyl having 2 to 5 carbon atoms, with preference given to halogen atom and alkyl having 1 to 5 carbon atoms, and more preference given to fluorine, chlorine and methyl. Examples of preferable $R^{11}$ include 4-fluorophenyl, 4-chlorophenyl, p-tolyl and 2-naphthyl.

The $C_1$–$C_4$ alkyl at $R^{12}$ and $R^{13}$ may be, respectively, for example, methyl, ethyl, propyl, isopropyl, butyl, isobutyl, sec-butyl or tert-butyl, with preference given to propyl, isopropyl and tert-butyl, and more preference given to isopropyl. It is preferable that one of $R^{12}$ and $R^{13}$ be hydrogen and the other be propyl, isopropyl, isobutyl or tert-butyl, with more preference given to $R^{12}$ being propyl, isopropyl, isobutyl or tert-butyl, and $R^{13}$ being hydrogen, with still more preference given to $R^{12}$ being isopropyl and $R^{13}$ being hydrogen. The ring having 3 to 7 carbon atoms, which is optionally formed by $R^{12}$ and $R^{13}$ may be, for example, cyclopropylidene, cyclobutylidene, cyclopentylidene, cyclohexylidene or cycloheptylidene, with preference given to cyclohexylidene.

The lower alkyl at $R^{11}$ may be linear, branched or cyclic alkyl having 1 to 6 carbon atoms, such as methyl, ethyl, propyl, isopropyl, butyl, isobutyl, sec-butyl, tert-butyl, pentyl, isopentyl, neopentyl, tert-pentyl, hexyl, 4-methylpentyl, 1,1-dimethylbutyl, 2,2-dimethylbutyl, 3,3-dimethylbutyl, 2-ethylbutyl and the like, with preference given to methyl and isobutyl.

The aryl which optionally substitutes said lower alkyl may be, for example, phenyl, 1-naphthyl or 2-naphthyl, with preference given to phenyl. The cycloalkyl which optionally substitutes said lower alkyl may be, for example, cyclopropane, cyclobutane, cyclopentane or cyclohexane, with preference given to cyclohexane. The aromatic heterocycle which optionally substitutes said lower alkyl may be, for example, heteromonocyclic residue and condensed heterocyclic residue substituted by oxygen, nitrogen or sulfur atom. Examples of heteromonocyclic residue include pyrolyl, furanyl, thiophenyl, oxazolyl, thiazolyl, imidazolyl, pyrazolyl, pyridyl and the like; and examples of condensed heterocyclic residue include indolyl, quinolyl, benzothiophenyl, benzofuranyl, indazolyl, quinazolynyl, phthaladinyl, quinoxalynyl and the like, with preference given to indolyl.

Examples of $R^{14}$ include isobutyl, benzyl, cyclohexylmethyl, indol-3-ylmethyl and the like.

The salts of the compound of the formula (VI) are preferably physiologically acceptable ones, such as salts with inorganic base, salts with organic base, salts with inorganic acid, salts with organic acid, salts with basic or acidic amino acid, and the like. Examples of preferable salts with inorganic base include alkali metal salts such as sodium salt and potassium salt; alkaline earth metal salts such as calcium salt and magnesium salt; and aluminum salt and ammonium salt. Examples of preferable salts with organic base include salts with trimethylamine, pyridine, picoline, ethanolamine, diethanolamine, triethanolamine, dicyclohexylamine, N,N-dibenzylethylenediamine and the like. Examples of preferable salts with inorganic acid include salts with hydrochloric acid, hydrobromic acid, nitric acid, sulfuric acid, phosphoric acid and the like. Examples of preferable salts with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like. Examples of preferable salts with basic amino acid include salts with arginine, lysine, ornithine and the like, and examples of preferable salts with acidic amino acid include salts with aspartic acid, glutamic acid and the like.

The compound (VI) can be produced, for example, by the following reactions,

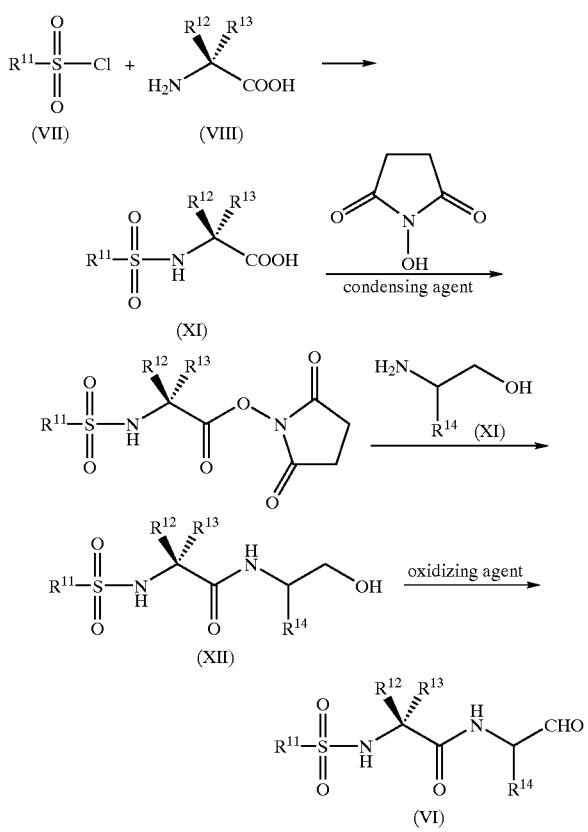

wherein each symbol is as defined above.

Sulfonyl chloride of the formula (VII) [hereinafter sometimes referred to as compound (VII)] may be, for example, naphthalenesulfonyl chloride, toluenesulfonyl chloride, fluorobenzenesulfonyl chloride, chlorobenzenesulfonyl chloride, bromobenzenesulfonyl chloride and benzenesulfonyl chloride.

The compound of the formula (VIII) [hereinafter sometimes referred to as compound (VIII)] may be, for example, glycine, alanine, valine, D-valine, norvaline, leucine, isoleucine, norleucine, tert-leucine, 1-aminocyclopropanecarboxylic acid, 1-aminocyclobutanecarboxylic acid, 1-aminocyclopentanecarboxylic acid, 1-aminocyclohexanecarboxylic acid and the like.

The reaction of compound (VII) and compound (VIII) can be carried out by a method generally known, such as Shotten-Baumann reaction.

The compound of the formula (IX) and N-hydroxysuccinimide may be dissolved in an organic solvent generally used, such as tetrahydrofuran, dichloromethane, chloroform and ethyl acetate, and condensed using a condensing agent. Examples of the condensing agent include N,N-dicyclohexyl carbodiimide, 1-ethyl-3-(3-dimethylaminopropyl)carbodiimide hydrochloride, and the like.

The amino alcohol of the formula (XI) [hereinafter sometimes referred to as compound (XI)] may be, for example, valinol, leucinol, D-leucinol, phenylalaninol, tryptophanol or (s)-2-amino-3-cyclohexyl-1-propanol.

The compound of the formula (X) and compound (XI) are, for example, dissolved in a solvent such as tetrahydrofuran, dichloromethane, chloroform and ethyl acetate, and are reacted in the presence of a base (e.g., triethylamine and pyridine).

The compound of the formula (XII) is oxidized with an oxidizing agent (e.g., sulfur trioxide-pyridine complex, oxalyl chloride and chromic acid-pyridine) to give a new compound (VI).

While the reaction temperature is not particularly limited, the reaction generally proceeds under cooling, at room temperature or under heating.

The structural formula of the compounds obtained in Examples to be mentioned later are shown in the following.

TABLE 3

| Com. No. | $R^{11}$ | $R^{12}$ | $R^{14}$ | * |
|---|---|---|---|---|
| 34 | 2-naphthyl | isopropyl | isobutyl | S |
| 35 | 4-fluorophenyl | isopropyl | isobutyl | S |
| 36 | 4-chlorophenyl | isopropyl | isobutyl | S |
| 37 | 4-tolyl | isopropyl | isobutyl | S |
| 38 | 2-naphthyl | tert-butyl | isobutyl | S |
| 40 | 4-fluorophenyl | butyl | isobutyl | S |
| 41 | 4-fluorophenyl | propyl | isobutyl | S |
| 42 | 2-naphthyl | tert-butyl | benzyl | S |
| 43 | 4-fluorophenyl | isopropyl | benzyl | S |
| 44 | 2-naphthyl | isopropyl | benzyl | S |
| 45 | 4-chlorophenyl | isopropyl | benzyl | S |
| 46 | 4-tolyl | isopropyl | benzyl | S |
| 48 | 4-chlorophenyl | isopropyl | —CH₂-(indol-3-yl) | S |
| 49 | 4-fluorophenyl | isopropyl | —CH₂-(indol-3-yl) | S |
| 51 | 2-naphthyl | tert-butyl | —CH₂-(indol-3-yl) | S |
| 52 | 4-fluorophenyl | isopropyl | cyclohexylmethyl | S |
| 53 | 2-naphthyl | isopropyl | cyclohexylmethyl | S |
| 54 | 4-chlorophenyl | isopropyl | cyclohexylmethyl | S |
| 56 | 4-fluorophenyl | isopropyl | isobutyl | R |

TABLE 4

| Com. No. | $R^{11}$ | $R^{14}$ | * |
|---|---|---|---|
| 39 | 4-fluorophenyl | isobutyl | S |
| 55 | 4-fluorophenyl | isobutyl | R |

TABLE 5

[Structure: R¹¹—S(O)₂—N(H)—C(cyclohexyl)(C(O)—N(H)—CH(S)(R¹⁴)—CHO)]

| Com. No. | R¹¹ | R¹⁴ |
| --- | --- | --- |
| 47 | 2-naphthyl | benzyl |
| 50 | 2-naphthyl | —CH₂-(indol-3-yl) |

Cysteine protease inhibitory compounds can be administered systemically or locally. For systemic administration, they are administered orally or parenterally by, for example, intravenous injection, subcutaneous injection, intramuscular injection and the like. For local administration, they are administered transdermally, transmucosally, intranasally, intraocularly or other route.

Cysteine protease inhibitory compounds can be used to formulate pharmaceutical compositions. Examples of compositions to be orally administered to human include powders, granules, tablets, capsules, syrups, liquids, and the like. When the composition is prepared into powders, granules, tablets and the like, optional pharmaceutical carriers suitable for preparing solid compositions, such as vehicles (e.g., starch, glucose, fruit sugar, sucrose and the like), lubricants (e.g., magnesium stearate), disintegrators (e.g., starch and crystalline cellulose), and binders (e.g., starch and gum arabic). The compositions may be coated with gelatin, sucrose and the like are admixed as appropriate. When the composition is syrup or liquid, for example, stabilizers (e.g., sodium edetate), suspending agents (e.g., gum arabic and carmellose), corrigents (e.g., simple syrup and glucose), aromatics and the like may be used as appropriate. A parenteral composition may be injections or suppositories. When the composition is an injection, for example, solvents (e.g., distilled water for injection), stabilizers (e.g., sodium edetate), isotonizing agents (e.g., sodium chloride, glycerine and mannitol), pH adjusting agents (e.g., hydrochloric acid, citric acid and sodium hydroxide), suspending agents (e.g., methyl cellulose) and the like may be used. When the composition is suppositories, for example, a base for suppositories such as cacao butter and macrogols, may be used as appropriate. Examples of compositions for external use include ointment, cream, lotion, collunarium, eye drop and the like. These compositions for external use may contain, in addition to said inhibitory compound, for example, known compounds such as ointment base (e.g., petrolatum and lanolin), solvent (e.g., physiological saline and purified water), stabilizer (e.g., sodium edetate and citric acid), wetting agent (e.g., glycerine), emulsifier (e.g., polyvinylpyrrolidone), suspending agent (e.g., hydroxypropylmethylcellulose and methylcellulose), surfactant (e.g., polysorbate 80 and polyoxyethylene hydrogenated castor oil), preservative (e.g., benzalkonium chloride, p-hydroxybenzoate and chlorobutanol), buffer (e.g., boric acid, sodium tetraborate, sodium acetate, citrate buffer and phosphate buffer), isotonizing agent (e.g., sodium chloride, glycerol and mannitol), pH adjusting agent (e.g., hydrochloric acid and sodium hydrochloride) and the like as appropriate.

The angiogenesis inhibitor of the present invention may contain other pharmaceutical ingredients such as antiinflammatory drug, antitumor drug and antimicrobial agent, and the like.

While the dose of the cysteine protease inhibitory compound may vary depending on target disease, symptom, administration target, administration route and the like, the amount per dose is generally 1–500 mg, preferably 10–200 mg by oral administration, and generally 0.1–100 mg, preferably 1–50 mg by injection. When the composition is administered locally, for example, an eye drop adjusted generally to 0.001–1.0 w/v %, preferably 0.01–0.5 w/vb %, is instilled to the eye by 20–50 μl at a time for 5 or 6 times a day.

The present invention is described in more detail by way of Examples and Experimental Examples in the following, which by no way limit the present invention.

The following Reference Examples, Examples and Experimental Examples are all intended to describe the present invention in further detail and should by no means be construed as defining the scope of the invention.

EXAMPLE 1

| (Tablet) | |
| --- | --- |
| E-64 | 30 mg |
| Lactose | 80 mg |
| Starch | 17 mg |
| Magnesium stearate | 3 mg |

Using the above ingredients as the material for one tablet, tablets are preared by a conventional method. Where necessary, sugar coating may be applied.

EXAMPLE 2

| (Injection) | |
| --- | --- |
| Leupeptin | 100 mg |
| Sodium chloride | 900 mg |
| 1N sodium hydroxide | q.s. |
| Distilled water for injection | total 100 ml |

The above ingredients are admixed by a conventional method to give injections.

EXAMPLE 3

| (Eye drop) | |
| --- | --- |
| 27 mer calpastatin peptide | 1 g |
| Boric acid | 0.7 g |
| Sodium tetraborate | q.s. |
| Sodium chloride | 0.5 g |
| Hydroxymethylcellulose | 0.1 g |
| EDTA sodium | 0.02 g |
| Benzalkonium chloride | 0.005 g |
| Sterile purified water | total 100 ml |

The above ingredients are admixed by a conventional method to give suspension for instillation.

Reference Example 1

To a solution of N-tert-butoxycarbonylphenylalanine (53 g, 0.2 mol) and p-nitrophenol (27.8 g, 0.2 mol) in ethyl acetate (200 ml) in an ice-water bath was dropwise added a solution of N,N'-dicyclohexylcarbodiimide (41.2 g, 0.2 mol) in ethyl acetate (100 ml), and the mixture was stirred in an ice-water bath for 3 hours and then at room temperature for 20 hours. The precipitated N,N'-dicyclohexylcarbodiurea was filtered off and the filtrate was concentrated under reduced pressure. The residue thus obtained was recrystallized from ethyl acetate-hexane to give N-tert-butoxycarbonylphenylalanine p-nitrophenyl ester [61.7 g, 80% (% by weight, hereinafter the same)].

Reference Example 2

To a solution of N-tert-butoxycarbonylleucine (6.94 g, 30 mmol) and N-hydroxysuccinimide (3.45 g, 30 mmol) in dioxane (50 ml) in an ice-water bath was dropwise added a solution of N-ethyl-N'-(3-dimethylaminopropyl) carbodiimide hydrochloride (5.75 g, 30 mmol) in dioxane, and the mixture was stirred in an ice-water bath for 20 minutes and then at room temperature for 24 hours. The reaction mixture was poured into cold water and extracted with ethyl acetate. The extract was washed with 10 w/v % aqueous citric acid solution, 10 w/v % aqueous sodium hydrogencarbonate solution, and saturated brine in the order mentioned, and the organic layer was dried over anhydrous magnesium sulfate and concentrated under reduced pressure. The residue was recrystallized from isopropyl ether to give N-tert-butoxycarbonylleucine N-hydroxysuccinimide ester (7.77 g, 78.9%).

Reference Example 3

To a solution of 1-(4-fluorophenyl)piperazine dihydrochloride (2.53 g, 10 mmol) in N,N-dimethylformamide (40 ml) were added triethylamine (2.8 ml, 20 mmol) and N-tert butoxycarbonylphenylalanine p-nitrophenyl ester (2.65 g, 10 mmol) in the order mentioned, and the mixture was stirred at room temperature overnight. The reaction mixture was poured into cold water and extracted with ethyl acetate. The extract was washed with 1 w/v % aqueous ammonia, saturated brine, 0.1N hydrochloric acid, saturated brine, saturated aqueous sodium hydrogencarbonate solution, and saturated brine in the order mentioned, and the organic layer was dried over anhydrous magnesium sulfate and further concentrated under reduced pressure. The residue was purified by silica gel column chromatography using chloroform-methanol (50:1, v/v) to give 1,1-dimethylethyl 2-(4-(4-fluorophenyl)-1-piperazinyl)-2-oxo-1-(phenylmethyl) ethylcarbamate (2.7 g, 92.2%) as colorless oil.

Reference Example 4

Using 1-(o-fluorophenyl)piperazine monohydrochloride instead of 1-(4-fluorophenyl)piperazine dihydrochloride, the procedure of Reference Example 3 was repeated to give 1,1-dimethylethyl-2-(4-(2-fluorophenyl)-1-piperazinyl)-2-oxo-1-(phenylmethyl)ethylcarbamate (1.89 g, 88.4%).

Reference Example 5

To a solution of 1-(4-fluorophenyl)piperazine dihydrochloride (0.91 g, 3 mmol) and N-tert-butoxycarbonylleucine N-hydroxysuccinimide ester (0.99 g, 3 mmol) in dichioromethene (50 ml) was added triethylamine (1.3 ml, 9 mmol), and the mixture was stirred at room temperature for 20 hours. The reaction mixture was washed with 0.1N hydrochloric acid, saturated aqueous sodium hydrogencarbonate solution, water, and saturated brine in the order mentioned, and the organic layer was dried over anhydrous magnesium sulfa and concentrated under reduced pressure. The residue was subjected to silica gel column chromatography using ethyl acetate-hexane (1:1, v/v) to give 1,1-dimethylethyl 2-(4-(4-fluorophenyl)-1-piperazinyl)-2-oxo-1-(2-methylpropyl)ethylcarbamate (1.05 g, 89.0%) as colorless oil.

Reference Example 6

Using 4-phenylpiperazine instead of 1-(4-fluorophenyl) piperazine dihydrochloride, the procedure of Reference Example 5 was repeated to give 1,1-dimethylethyl 2-(4-phenyl-1-piperazinyl)-2-oxo-1-(2-methylpropyl) ethylcarbamate (7.99 g, 99%).

Reference Example 7

Using 1-dimethylsulfamoylpiperazine instead of 1-(4-fluorophenyl)piperazine dihydrochloride, the procedure of Reference Example 5 was repeated to give 1,1-dimethylethyl 2-(4-dimethylsulfamoyl-1-piperazinyl)-2-oxo-1-(2-methylpropyl)ethylcarbamate (7.19 g, 88.4%).

Reference Example 8

Using p-toluenesulfonylpiperazine instead of 1-(4-fluorophenyl)piperazine dihydrochloride, the procedure of Reference Example 5 was repeated to give 1,1-dimethylethyl 2-(4-(4-methylphenylsulfonyl)-1-piperazinyl)-2-oxo-1-(2-methylpropyl)ethylcarbamate (6.95 g, 79.4%).

Reference Example 9

Using 1-(2-chlorophenyl)piperazine instead of 1-(4-fluorophenyl)piperazine dihydrochloride, the procedure of Reference Example 5 was repeated to give 1,1-dimethylethyl 2-(4-(2-chlorophenyl)-1-piperazinyl)-2-oxo-1-(2-methylpropyl)ethylcarbamate (5.70 g, 95.5%).

Reference Example 10

Using 1-(m-chlorophenyl)piperazine monohydrochloride instead of 1-(4-fluorophenyl)piperazine dihydrochioride, the procedure of Reference Example 5 was repeated to give 1,1-dimethylethyl 2-(4-(3-chlorophenyl)-1-piperazinyl)-2-oxo-1-(2-methylpropyl)ethylcarbamate (2.63 g, 88.4%).

Reference Example 11

Using 1-(4-chlorophenyl)piperazine monohydrochloride instead of 1-(4-fluorophenyl)piperazine dihydrochioride, the procedure of Reference Example 5 was repeated to give 1,1-dimethylethyl 2-(4-(4-chlorophenyl)-1-piperazinyl)-2-oxo-1-(2-methylpropyl)ethylcarbamate (2.83 g, 94.8%).

Reference Example 12

Using N-(p-methoxyphenyl)piperazine succinate instead of 1-(4-fluorophenyl)piperazine dihydrochloride, the procedure of Reference Example 5 was repeated to give 1,1-dimethylethyl 2-(4-(4-methoxyphenyl)-1-piperazinyl)-2-oxo-1-(2-methylpropyl)ethylarbamate (2.73 g, 92.3%).

Reference Example 13

To a solution of 1,1-dimethylethyl 2-(4-(4-fluorophenyl)-1-piperazinyl)-2-oxo-1-(phenylmethyl)ethylcarbamate (2.7 g, 6.3 mmol) in ethyl acetate (20 mmol) under ice-cooling was dropwise added 4N HCl/ethyl acetate (20 ml), and the mixture was stirred at room temperature overnight. The resulting crystals were recovered by filtration and recrystallized from ethanol-diethyl ether to give 1-(2-amino-1-oxo-3-phenylpropyl)-4-(4-fluorophenyl)piperazine hydrochloride (2.2 g, 96.1%) as pale-yellow crystals.

Reference Example 14

Using 1,1-dimethylethyl 2-(4-(2-fluorophenyl)-1-piperazinyl)-2-oxo-1-(phenylmethyl)ethylcarbAmate instead of 1,1-dimethylethyl 2-(4-(4-fluorophenyl)-1-piperazinyl)-2-oxo-1-(phenylmethyl)ethylcarbamate, the procedure of Reference Example 13 was repeated to give 1-(2-amino-1-oxo-3-phenylpropyl)-4-(2-fluorophenyl) piperazine hydrochloride (1.3 g, 99.1%) as white crystals.

Reference Example 15

Using 1,1-dimethylethyl 2-(4-(2-fluorophenyl)-1-piperazinyl)-2-oxo-1-(2-methylpropyl)ethylcarbamate instead of 1,1-dimethylethyl 2-(4-(4-fluorophenyl)-1-piperazinyl)-2-oxo-1-(phenylmethyl)ethylcabarnate, the procedure of Reference Example 13 was repeated to give 1-(2-amino-4-methyl-1-oxopentyl)-4-(4-fluorophenyl) piperazine hydrochloride (0.56 g, 70.4%) as white crystals.

Reference Example 16

Using 1.1-dimethylethyl 2-(4-phenyl-1-piperazinyl)-2-oxo-1-(2-methylpropyl)ethylcarbamate instead of 1,1-dimethylethyl 2-(4-(4-fluorophenyl)-1-piperazinyl)-2-oxo-1-(phenylmethyl)ethylcarbamate, the procedure of Reference Example 13 was repeated to give 1-(2-amino-4-methyl-1-oxopentyl)-4-phenylpiprazine hydrochloride (6.5 g, 99.2%) as white crystals.

Reference Example 17

Using 1,1-dimethylethyl 2-(4-dimethylsulfamoyl-1-piperazinyl)-2-oxo-1-(2-methylpropyl)ethylcarbamate instead of 1,1-dimethylethyl 2-(4-(4-fluorophenyl)-1-piperazinyl)-2-oxo-1-(phenylmethyl)ethylcarbamate, the procedure of Refers Example 13 was repeated to give 1-(2-amino-4-methyl-1-oxopentyl)-4-dimethysulfamoylpiperazine hydrochloride (5.0 g, 83.3%) as white crystals.

Reference Example 18

Using 1,1-dimethylethyl 2-(4-(4-methylphenylsulfonyl)-1-piperazinyl)-2-oxo-1-(2-methylpropyl)ethylcarbamate instead of 1,1-dimethylethyl 2-(4-(4-fluorophenyl)-1-piperazinyl)-2-oxo-1-(phenylmethyl)ethylcarbamate, the procedure of Reference Example 13 was repeated to give 1-(2-amino-4-methyl-1-oxopentyl)-4-(4-methylphenylsulfonyl)piperazine hydrochloride (4.83 g, 78.4%) as white crystals.

Reference Example 19

Using 1,1-dimethylethyl 2-(4-(2-chlorophenyl)-1-piperazinyl)-2-oxo-1-(2-methylpropyl)ethylcabmate instead of 1,1-dimethylethyl 2-(4-(4-fluorophenyl)-1-piperazinyl-2-oxo-1-(phenylmethyl)ethylcarbamate, the procedure of Reference Example 13 was repeated to give 1-(2-amino-4-methyl-1-oxopentyl)-4-(2-chorophenyl)piperazine hydrochloride (1.54 g, 62.6%) as white crystals.

Reference Example 20

Using 1,1-dimethylethyl 2-(4-(3-chlorophenyl)-1-piperazinyl)-2-oxo-1-(2-methylpropyl)ethylcarbamate instead of 1,1-dimethylethyl 2-(4-(4-fluorophenyl)-1-piperazinyl)-2-oxo-1-(phenylmethyl)ethylcarbamate, the procedure of Reference Example 13 was repeated to give 1-(2-amino-4-methyl-1-oxopentyl)-4-(3-chlorophenyl) piperazine hydrochloride (1.40 g, 65.7%) as white crystals.

Reference Example 21

Using 1,1-dimethylethyl 2-(4-(4-chlorophenyl)-1-piperazinyl)-2-oxo-1-(2-methylpropyl)ethylcarbamate instead of 1,1-dimethylethyl 2-(4-(4-fluorophenyl)-1-piperazinyl)-2-oxo-1-(phenylmethyl)ethylcarbamate, the procedure of Reference Example 13 was repeated to give 1-(2-amino-4-methyl-1-oxopentyl)-4-(4-chlorophenyl) piperazine hydrochloride (1.50 g, 65.3%) as white crystals.

Reference Example 22

Using 1,1-dimethylethyl 2-(4-(4-methoxyphenyl)-1-piperazinyl)-2-oxo-1-(2-methylpropyl)ethylcarbamate instead of 1,1-dimethylethyl 2-(4-(4-fluorophenyl)-1-piperazinyl)-2-oxo-1-(phenylmethyl)ethylcarbamate, the procedure of Reference Example 13 was repeated to give 1-(2-amino-4-methyl-1-oxopentyl)-4-(4-methoxyphenyl) piperazine hydrochloride (2.21 g, 87.4%) as white crystals.

Reference Example 23

To a solution of N-tert-butoxycarbonyl-L-valine (2.27 g, 10 mmol) and 1-(2-chlorophenyl)piperazine (2.00 g, 10 mmol) in N,N-dimethylformamide (50 ml) under ice-cooling was dropwise added a solution of 1-ethyl-3-(3-dimethylaminopropyl)carbodiimide hydrochloride (2.2 g, 11 mmol) and 1-hydroxybenzotriazole (1.5 g, 11 mmol) in dichloromethane (50 ml), and the reaction mixture was stirred at room temperature for 15 hours. The dichloromethane was then distilled off under reduced pressure and ethyl acetate (200 ml) was added to the residue. The ethyl acetate layer was washed successively with 10 w/v % aqueous citric acid solution, saturated aqueous sodium hydrogen carbonate solution, and saturated brine in the order mentioned and dried over anhydrous sodium sulfate. The solvent was then distilled off and the residue was subjected to silica gel chromatography. Elution with ethyl acetate-n-hexane (1:2, v/v) gave 1,1-dimethylethyl 2-(4-(2-chlorophenyl)piperazinyl)-2-oxo-(s)-1-(2-propyl) ethylcarbamate. This colorless oil was dissolved in ethyl acetate (50 ml), and 4N HCl/ethyl acetate (50 ml) was added dropwise under ice-cooling. The mixture was stirred at room temperature for 3 hours. The reaction product was filtered and washed with ethyl acetate-n-hexane (1:1, v/v) to give 1-((s)-2-amino-3-methyl-1-oxobutyl)-4-(2-chlorophenyl) piperazine hydrochloride (3.32 g, 95.8%) as colorless crystals.

Reference Example 24

Starting with N-tert-butoxycarbonylglycine, the procedure of Reference Example 23 was repeated to give 1-(2-amino-1-oxoethyl)-4-(2-chlorophenyl)piperazine hydrochloride (2.4 g, 90.4%) as colorless crystals.

Reference Example 25

Starting with N-tert-butoxycarbonyl-L-alanine, the procedure of Reference Example 23 was repeated to give 1-((s)-2-amino-1-oxopropyl)-4-(2-chlorophenyl)piperazine hydrochloride (1.7 g, 58.8%) as colorless crystals.

Reference Example 26

Starting with N-tert-butoxycarbonyl-L-isoleucine, the procedure of Reference Example 23 was repeated to give 1-((s)-2-amino-3-methyl-1-oxo-pentyl)-4-(2-chlorophenyl) piperazine hydrochloride (3.4 g, 90.2%) as colorless crystals.

Reference Example 27

Starting with N-tert-butoxycarbonyl-β-alanine, the procedure of Reference Example 23 was repeated to give 1-(3-amino-1-oxopropyl)-4-(2-chlorophenyl)piperazine hydrochloride (2.9 g, 90.0%) as colorless crystals.

Reference Example 28

Starting with N-tert-butoxycarbonylsarcosine, the procedure of Reference Example 23 was repeated to give 1-(2-methylamino-1-oxoethyl)-4-(2-chlorophenyl)piperazine hydrochloride (3.0 g, 93.3%) as colorless crystals.

Reference Example 29

Starting with N-tert-butoxycarbonyl-L-proline, the procedure of Reference Example 23 was repeated to give 1-(1-(2-pyrrolidinyl)-1-oxomethyl)-4-(2-chlorophenyl) piperazine hydrochloride (4.3 g, 98.0%) as colorless crystals.

Reference Example 30

Starting with N-tert-butoxycarbonyl-(s)-acetamidomethyl)-L-cysteine, the procedure of Reference Example 23 was repeated to give 1-((s)-2-amino-3-(acetylaminomethylthio)-1-oxopropyl)-4-(2-chlorophenyl) piperazine hydrochloride (4.0 g, 95.9%) as colorless crystals.

Reference Example 31

Starting with N-tert-butoxycarbonyl-L-methionine, the procedure of Reference Example 23 was repeated to give 1-((s)-2-amino-4-methylthio-1-oxo-butyl)-4-(2-chlorophenyl)piperazine hydrochloride (3.7 g, 97.1%) as colorless crystals.

Reference Example 32

Starting with N-tert-butoxycarbonyl-L-glutamine, the procedure of Reference Example 23 was repeated to give 1-((s)-2-amino-4-carbamoyl-1-oxo-butyl)-4-(2-chlorophenyl)piperazine hydrochloride (2.7 g, 60.7%) as colorless crystals.

EXAMPLE 4

To a solution of 1-(2-amino-1-oxo-3-phenylpropyl)-4-(4-fluorophenyl)piperazine hydrochloride (1.82 g, 5 mmol) in N,N-dimethylformamide (20 ml) was added triethylamine (0.697 ml, 5 mmol), and the mixture was stirred at room temperature for 10 minutes. To the reaction mixture was added ethyl p-nitrophenyl L-trans-epoxysuccinate (1.41 g, 5 mmol), synthesized in accordance with the method of Tamai et al. [Chem. Pharm. Bull., 35, 1098 (1987)], and the mixture was stirred at room temperature for 20 hours. The reaction mixture was poured into cold water and extracted with ethyl acetate. The extract was washed successively with 1 w/v % aqueous ammonia, saturated brine, 0.1N hydrochloric acid, saturated brine, saturated aqueous sodium hydrogen-carbonate solution, and saturated brine in the order mentioned, and the organic layer was dried over anhydrous magnesium sulfate and concentrated under reduced pressure. The residue was subjected to silica gel column chromatography, elution being carried out with ethyl acetate-hexane (1:1, v/v) to give ethyl (2s,3s)-3-[[[[(1s)-1-[[4-(4-fluorophenyl)-1-piperadinyl]carbonyl]-2-phenyl] ethyl]amino]carbonyl]oxiranecarboxylate (1.2 g, 51.1%; Compound 1).

$^1$H NMR (CDCl$_3$) δ: 1.31 (t, 3H, J=7.0 Hz, —C—CH$_3$), 2.42–2.50 (m, 1H, piperazine ring), 2.83–2.94 (m, 2H, piperazine ring), 3.00 (d, 2H, J=7.6 Hz, ph-CH$_2$—C—), 2.97–3.07 (m, 1H, piperazine ring), 3.14–3.22 (m, 1H, piperazine ring), 3.35 (d, 1H, J=1.9 Hz, epoxy ring), 3.43–3.52 (m, 1H, piperazine ring), 3.64 (d, 1H, J=1.9 Hz, epoxy ring), 3.71 (t, 2H, J=5.4 Hz, piperazine ring), 4.25 (dq, 2H, J=7.3, 2.6 Hz, —O—CH$_2$—C), 5.18 (q, 1H, J=5.3 Hz —N—CH—CO), 6.75–6.83 (m, 2H, aromatic), 6.91–7.04 (m, 2H, aromatic, 1H, NH), 7.17–7.34 (m, 5H, aromatic).

EXAMPLE 5

Using 1-(2-amino-1-oxo-3-phenylpropyl)-4-(2-fluorophenyl)piperazine hydrochloride instead of 1-(2-amino-1-oxo-3-phenylpropyl)-4-(4-fluorophenyl)piperazine hydrochloride, the procedure of Example 4 was repeated to give ethyl (2s, 3s)-3-[[[[(1s)-1-[[4-(2-fluorophenyl)-1-piperazinyl]carbonyl]-2-phenyl]ethyl]amino]carbonyl] oxiranecaboxylate (0.83 g, 58.6%; Compound 2).

$^1$H NMR (CDCl$_3$) δ: 1.31 (t, 3H, J=7.1 Hz, —C—CH$_3$), 2.42–2.49 (m, 1H, piperazine ring), 2.72–2.90 (m, 2H, piperazine ring), 3.02 (d, 2H, J=8.3 Hz, ph-CH$_2$—C—), 2.94–3.10 (m, 1H, piperazine ring), 3.17–3.29 (m, 1H, piperazine ring), 3.36 (d, 1H, J=1.7 Hz, epoxy ring), 3.44–3.57 (m, 1H, piperazine ring), 3.65 (d, 1H, J=1.3 Hz, epoxy ring), 3.66–3.80 (m, 2H, piperazine ring), 4.25 (dq, 2H, J=7.1, 2.3 Hz, —O—CH$_2$—C), 5.19 (q, 1H, J=7.6 Hz, —N—CH—CO), 6.8 (t, 1H, J=8.3 Hz, —NH—), 6.93–7.11 (m, 4H, aromatic), 7.18–7.34 (m, 5H, aromatic).

EXAMPLE 6

Using 1-(2-amino-4-methyl-1-oxopentyl)-4-(4-fluorophenyl)piperazine hydrochloride instead of 1-(2-amino-1-oxo-3-phenylpropyl)-4-(4-fluorophenyl)piperazine hydrochloride, the procedure of Example 4 was repeated to give ethyl (2s,3s)-3-[[[[(1s)-1-[[4-(4-fluorophenyl)-1-piperazinyl]carbonyl]-3-methyl]butyl]amino]carbonyl] oxiranecarboxylate (0.30 g, 45.6%; Compound 3).

$^1$H NMR (CDCl$_3$) δ: 0.93 (d, 3H, J=6.3 Hz, —C—CH$_3$), 1.00 (d, 3H, J=6.3 Hz, —C—CH$_3$), 1.32 (t, 3H, J=7.3 Hz, —C—CH$_3$), 1.40–1.63 (m, 3H, —C—CH$_2$—CH—C$_2$), 3.06–3.15 (m, 4H, piperazine ring), 3.49 (d, 1H, J=1.7 Hz, epoxy ring), 3.60–3.89 (m, 4H, piperazine ring), 3.68 (d, 1H, J=1.7 Hz, epoxy ring), 4.26 (dq, 2H, J=7.3, 3.3 Hz, —O—CH$_2$—C), 5.03 (dt, 1H, J=8.91, 4.3 Hz, —N—CH—CO), 6.85–7.03 (m, 5H, aromatic and —NH).

EXAMPLE 7

Using 1-(2-amino-4-methyl-1-oxopentyl)-4-phenylpiperazine hydrochloride instead of 1-(2-amino-1-oxo-3-phenylpropyl)-4-(4-fluorophenyl)piperazine hydrochloride, the procedure of Example 4 was repeated to give ethyl (2s,3s)-3-[[[[(1s)-1-[(4-phenyl-1-piperazinyl) carbonyl]-3-methyl]butyl]amino]carbonyl] oxiranecarboxylate (3.96 g, 63.3%; Compound 4).

$^1$H NMR (CDCl$_3$) δ: 0.93 (d, 3H, J=6.3 Hz, —C—CH$_3$), 1.00 (d, 3H, J=6.3 Hz, —C—CH$_3$), 1.32 (t, 3H, J=7.3 Hz, —C—CH$_3$), 1.40–1.63 (m, 3H, —C—CH$_2$—CH—C$_2$, 3.16–3.24 (m, 4H, piperazine ring), 3.49 (d, 1H, J=1.7 Hz, epoxy ring), 3.60–3.89 (m, 4H, piperazine ring), 3.68 (d, 1H, J=1.7 Hz, epoxy ring), 4.26 (dq, 2H, J=7.3, 3.3 Hz, —O—CH$_2$—C), 5.03 (dt, 1H, J=8.9, 4.3 Hz, —N—CH—CO), 6.90–6.95 (m, 4H, aromatic and —NH), 7.25–7.33 (m, 2H, aromatic).

EXAMPLE 8

Using 1-(2-amino-4-methyl-1-oxopentyl)-4-dimethylsulfamoylpiperazine hydrochloride instead of 1-(2-amino-1-oxo-3-phenylpropyl)-4-(4-fluorophenyl)piperazine hydrochloride, the procedure of Example 4 was repeated to give ethyl (2s,3)-3-[[[[(1s)-1-[(4-dimethylsulfamoyl-1-piperazinyl)carbonyl]-3-methyl]butyl]amino]carbonyl] oxiranecarboxylate (3.7 g, 82.6%; Compound 5).

$^1$H NMR (CDCl$_3$) δ: 0.92 (d, 3H, J=6.3 Hz, —C—CH$_3$), 0.89 (d, 3H, J=6.3 Hz, —C—CH$_3$), 1.32 (t, 3H, J=7.3 Hz, —C—CH$_3$), 1.38–1.60 (m, 3H, —C—CH$_2$—CH—C$_2$), 2.85 (s, 6H, —N—CH$_3$), 3.15–3.38 (m, 4H, piperazine ring), 3.48 (d, 1H, J=1.7 Hz, epoxy ring), 3.52–3.68 (m, 3H, piperazine ring), 3.67 (d, 1H, J=1.7 Hz, epoxy ring), 3.79–3.87 (m, 1H, piperazine ring), 4.27 (dq, 2H, J=7.3, 4.0 Hz, —O—CH$_2$—C), 4.96 (dt, 1H, J=8.9, 4.3 Hz, —N—CH—CO), 6.90 (d, 1H, J=8.6 Hz, —NH—).

EXAMPLE 9

Using 1-(2-amino-4-methyl-1oxopentyl)-4-(4-methylphenylsulfonyl)piperazine hydrochloride instead of 1-(2-amino-1-oxo-3-phenylpropyl)-4-(4-fluorophenyl) piperazine hydrochloride, the procedure of Example 4 was repeated to give ethyl (2s,3s)-3-[[[[(2s)-1-[[4-(4-methylphenylsulfonyl)-1-piperazinyl]carbonyl]-3-methyl]butyl]amino]carbonyl]oxiranecarboxylate (4.31 g, 95.1%; Compound 6).

$^1$H NMR (CDCl$_3$) δ: 0.87 (d, 3H. J=6.3 Hz, —C—CH$_3$), 0.94 (d, 3H, J=6.3 Hz, —C—CH$_3$), 1.30 (t, 3H, J=7.3 Hz, —C—CH$_3$), 1.31–1.55 (m, 3H, —C—CH$_2$—CH—C$_2$), 2.45 (s, 6H, -ph-CH$_3$), 2.70–2.84 (m, 2H, piperazine ring), 3.22–3.54 (m, 4H, piperazine ring), 3.43 (d, 1H, J=1.7 Hz, epoxy ring), 3.61 (d, 1H, J=2.0 Hz, epoxy ring), 3.68–3.78 (m, 1H, piperazine ring), 3.96–4.06 (m, 1H, piperazine ring), 4.25 (dq, 2H, J=7.3, 4.0 Hz, —O—CH$_2$—C), 4.87 (dt, 1H, J=9.2, 4.0 Hz, —N—CH—CO), 6.81 (d, 1H, J=8.6 Hz, —NH—), 7.35 (d, 2H, J=7.9 Hz, aromatic), 7.63 (d, 2H, J=8.3 Hz, aromatic).

EXAMPLE 10

Using 1-(2-amino-4-methyl-1-oxopentyl)-4-(2-chlorophenyl)piperazine hydrochloride instead of 1-(2-amino-1-oxo-3-phenylpropyl)-4-(4-fluorophenyl)piperazine hydrochloride, the procedure of Example 4 was repeated to give ethyl (2s,3s)-3-[[[[(1s)-1-[[4-(2-chlorophenyl)-1-piperazinyl]carbonyl]-3-methyl]butyl]amino]carbonyl] oxiranecarboxylate (0.65 g, 35.9%; Compound 7).

$^1$H NMR (CDCl$_3$) δ: 0.93 (d, 3H, J=6.3 Hz, —C—CH$_3$), 1.01 (d, 3H, J=6.3 Hz, —C—CH$_3$), 1.32 (t, 3H, J=7.3 Hz, —C—CH$_3$), 1.41–1.61 (m, 3H, —C—CH$_2$—CH—C$_2$), 2.96–3.10 (m, 4H, piperazine ring), 3.49 (d, 1H, J=2.0 Hz, epoxy ring), 3.61–3.81 (m, 3H, piperazine ring), 3.68 (d, 1H, J=2.0 Hz, epoxy ring), 3.90–3.98 (m, 1H, piperazine ring), 4.27 (dq, 2H, J=7.3, 4.0 Hz, —O—CH$_2$—C), 5.03 (dt, 1H, J=8.9, 4.3 Hz, —N—CH—CO), 6.91 (d, 1H, J=8.6 Hz, —NH—), 7.00–7.06 (m, 2H, aromatic), 7.21–7.27 (m, 1H, aromatic), 7.37–7.41 (m, 1H, aromatic).

EXAMPLE 11

Using 1-(2-amino-4-methyl-1-oxopentyl)-4-(3-chlorophenyl)piperazine hydrochloride instead of 1-(2amino1-oxo-3-phenylpropyl)-4-(4-fluorophenyl) piperazine hydrochloride, the procedure of Example 4 was repeated to give ethyl (2s,3s)-3-[[[[(1s)-1-[[4-(3-chlorophenyl)-1-piperazinyl]carbonyl]-3-methyl]butyl] amino]carbonyl]oxiranecarboxylate (1.24 g, 68.4%; Compound 8).

$^1$H NMR (CDCl$_3$) δ: 0.93 (d, 3H, J=6.3 Hz, —CH—CH$_3$), 1.00 (d, 3H, J=6.3 Hz, —C—CH$_3$), 1.32 (t, 3H, J=7.3 Hz, —C—CH$_3$), 1.42–1.63 (m, 3H, —C—CH$_2$—CH—C$_2$), 3.17–3.25 (m, 4H, piperazine ring), 3.48 (d, 1H, J=2.0 Hz, epoxy ring), 3.60–3.90 (m, 4H, piperazine ring), 3.67 (d, 1H, J=2.0 Hz, epoxy ring), 4.27 (dq, 2H, J=7.3, 4.0 Hz, —O—CH$_2$—C), 5.02 (dt, 1H, J=8.9, 4.3 Hz, —N—CH—CO), 6.77–6.81 (m, 1H, aromatic), 6.86–6.89 (m, 3H, aromatic and —NH), 7.16–7.22 (m, 1H, aromatic).

EXAMPLE 12

Using 1-(2-amino-4-methyl-1-oxopentyl)-4-(4-chlorophenyl)piperazine hydrochloride instead of 1-(2-amino-1-oxo-3-phenylpropyl)-4-(4-fluorophenyl)piperazine hydrochloride, the procedure of Example 4 was repeated to give ethyl (2s,3s)-3-[[[[(1s)-1-[[4-(4-chlorophenyl)-1-piperazinyl]carbonyl]-3-methyl]butyl]amino]carbonyl] oxiranecarboxylate (0.55 g, 27.1%; Compound 9).

$^1$H NMR (CDCl$_3$) δ: 0.93 (d, 3H, J=6.3 Hz, —C—CH$_3$), 1.0 (d, 3H, J=6.3 Hz, —C—CH$_3$), 1.32 (t, 3H, J=7.3 Hz, —C—CH$_3$), 1.42–1.63 (m, 3H, —C—CH$_2$—CH—C$_2$), 3.12–3.20 (m, 4H, piperazine ring), 3.48 (d, 1H, J=2.0 Hz, epoxy ring), 3.60–3.90 (m, 4H, piperazine ring), 3.67 (d, 1H, J=2.0 Hz, epoxy ring), 4.27 (dq, 2H, J=7.3, 4.0 Hz, —O—CH$_2$—C), 5.02 (dt, 1H, J=8.9, 4.3 Hz, —N—CH—CO), 6.83–6.87 (m, 2H, aromatic), 6.90 (d, 1H, J=9.9 Hz, —NH), 7.21–7.3 (m, 2H, aromatic).

EXAMPLE 13

Using 1-(2-amino-4-methyl-1-oxopentyl)-4-(4-methoxyphenyl)piperazine hydrochloride instead of 1-(2-amino-1-oxo-3-phenylpropyl)-4-(4-fluorophenyl)piperazine hydrochloride, the procedure of Example 4 was repeated to give ethyl (2s,3s)-3-[[[[(1s)-1-[[4-(4-methoxyphenyl-1-piperazinyl]carbonyl]-3-methyl]butyl]amino]carbonyl] oxiranecarboxylate (0.94 g, 65.2%; Compound 10).

$^1$H NMR (CDCl$_3$) δ: 0.92 (d, 3H, J=6.6 Hz, —C—CH$_3$), 1.00 (d, 3H, J=6.3 Hz, —C—CH$_3$), 1.32 (t, 3H, J=7.3 Hz, —C—CH$_3$), 1.40–1.60 (m, 3H, —C—CH$_2$—CH—C$_2$), 3.03–3.11 (m, 4H, piperazine ring), 3.49 (d, 1H, J=2.0 Hz, epoxy ring), 3.60–3.88 (m, 4H, piperazine ring), 3.67 (d, 1H, J=2.0 Hz, epoxy ring), 3.78 (s, 3H, —O—CH$_3$), 4.27 (dq, 2H, J=7.3, 4.0 Hz, —O—CH$_2$—C), 5.03 (dt, 1H, J=8.9, 4.3 Hz, —N—CH—CO), 6.83–6.96 (m, 5H, aromatic and —NH).

EXAMPLE 14

Using 1-((s)-2-amino-3-methyl-1-oxobutyl)-4-(2-chlorophenyl)piperazine hydrochloride instead of 1-(2-amino-1-oxo-3-phenylpropyl)-4-(4-fluorophenyl)piperazine hydrochloride, the procedure of Example 4 was repeated to give ethyl (2s,3s)-3-[[[[(1s)-1-[[4-(2-chlorophenyl)-1-piperazinyl]carbonyl]-2-methyl]propyl]amino]carbonyl] oxiranecarboxylate (1.3 g, 57.4%) as colorless oil.

EXAMPLE 15

Using 1-(2-amino-1-oxoethyl)-4-(2-chlorophenyl) piperazine hydrochloride instead of 1-(2-amino-1-oxo-3-phenylpropyl)-4-(4-fluorophenyl)piperazine hydrochloride, the procedure of Example 4 was repeated to give ethyl (2s,3s)-3-[[[[4-(2-chlorophenyl)-1-piperazinyl]carbonyl]methyl]amino]carbonyl]oxiranecarboxylate (1.75 g, 53.5%) as colorless oil.

EXAMPLE 16

Using 1-((s)-2-amino-1-oxopropyl)-4-(2-chlorophenyl)piperazine hydrochloride instead of 1-(2-amino-1-oxo-3-phenylpropyl)-4-(4-fluorophenyl)piperazine hydrochloride, the procedure of Example 4 was repeated to give ethyl (2s,3s)-3-[[[(1s)-1-[[4-(2-chlorophenyl)-1-piperazinyl]carbonyl]ethyl]amino]carbonyl]oxiranecarboxylate (1.23 g, 55.0%) as colorless oil.

EXAMPLE 17

Using 1-((s)-2-amino-3-methyl-1-oxopentyl)-4-(2-chlorophenyl)piperazine hydrochloride instead of 1-(2-amino-1-oxo-3-phenylpropyl)-4-(4-fluorophenyl)piperazine hydrochloride, the procedure of Example 4 was repeated to give ethyl (2s,3s)-3-[[[[(1s)-1-[[4-(2-chlorophenyl)-1-piperazinyl]carbonyl]-2-methyl]butyl]amino]carbonyl]oxiranecarboxylate (1.48 g, 56.6%) as colorless oil.

EXAMPLE 18

Using 1-(3-amino-1-oxopropyl)-4-(2-chlorophenyl)piperazine hydrochloride instead of 1-(2-amino-1-oxo-3-phenylpropyl)-4-(4-fluorophenyl)piperazine hydrochloride, the procedure of Example 4 was repeated to give ethyl (2s,3s)-3-[[[2-[[4-(2-chlorophenyl)-1-piperazinyl]carbonyl]ethyl]amino]carbonyl]oxiranecarboxylate (1.16 g, 52.9%) as colorless oil.

EXAMPLE 19

Using 1-(2-methylamino-1-oxoethyl)-4-(2-chlorophenyl)piperazine hydrochloride instead of 1-(2-amino-1-oxo-3-phenylpropyl)-4-(4-fluorophenyl)piperazine hydrochloride, the procedure of Example 4 was repeated to give ethyl (2s,3s)-3-[[[[N-[[4-(2-chlorophenyl-1-piperazinyl]carbonyl]methyl]-N-methyl]amino]carbonyl]oxiranecarboxylate (1.55 g, 76.7%) as colorless oil.

EXAMPLE 20

Using 1-(1-(2-pyrrolidinyl)-1-oxomethyl)-4-(2-chlorophenyl)piperazine hydrochloride instead of 1-(2-amino-1-oxo-3-phenylpropyl)-4-(4-fluorophenyl)piperazine hydrochloride, the procedure of Example 4 was repeated to give ethyl (2s,3s)-3-[[(2s)-2-[[4-(2-chlorophenyl)-1-piperazinyl]carbonyl]-1-pyrrolidinyl]carbonyl]oxiranecarboxylate (1.42 g, 49.9%) as colorless oil.

EXAMPLE 21

Using 1-((s)-2-amino-3-(acetylaminomethylthio)-1-oxopropyl)-4-(2-chlorophenyl)piperazine hydrochloride instead of 1-(2-amino-1-oxo-3-phenylpropyl)-4-(4-fluorophenyl)piperazine hydrochloride, the procedure of Example 4 was repeated to give ethyl (2s,3s)-3-[[[[(1s)-1-[[4-(2-chlorophenyl)-1-piperazinyl]carbonyl]-2-acetylaminomethylthio]ethyl]amino]carbonyl]oxiranecarboxylate (1.19 g, 43.7%) as colorless oil.

EXAMPLE 22

Using 1-((s)-2-amino-4-methylthio-1-oxobutyl)-4-(2-chlorophenyl)piperazine hydrochloride instead of 1-(2-amino-1-oxo-3-phenylpropyl)-4-(4-fluorophenyl)piperazine hydrochloride, the procedure of Example 4 was repeated to give ethyl (2s,3s)-[[[[(1s)-1-[[4-(2-chlorophenyl-1-piperazinyl]carbonyl]-4-methylthio]butyl]amino]carbonyl]oxiranecarboxylate (1.54 g, 61.5%) as colorless oil.

EXAMPLE 23

Using 1-((s)-2-amino-4-carbamoyl-1-oxobutyl)-4-(2-chlorophenyl)piperazine hydrochloride instead of 1-(2-amino-1-oxo-3-phenylpropyl)-4-(4-fluorophenyl)piperazine hydrochloride, the procedure of Example 4 was repeated to give ethyl (2s,3s)-3-[[[[(1s)-1-[[4-(2-chlorophenyl)-1-piperazinyl]carbonyl]-3-carbamoyl]propyl]amino]carbonyl]oxiranecarboxylate (0.2 g, 5.8%) as colorless oil.

EXAMPLE 24

To a solution of ethyl (2s,3s)-3-[[[[(1s)-1-[[4-(4-fluorophenyl-1-piperazinyl]carbonyl]-2-phenyl]ethyl]amino]carbonyl]oxiranecarboxylate (0.5 g, 1.06 mmol) in ethanol (20 ml) was added 0.1N sodium hydroxide/ethanol (16 ml) under ice-cooling and the mixture was stirred at room temperature for 20 hours. The reaction mixture was poured into cold water and acidified with 1N hydrochloric acid and the resulting white precipitate was recovered by filtration and dried. This precipitate was recrystallized from ethyl acetate-hexane to give (2s,3s)-3-[[[[(1s)-1-[[4-(4-fluorophenyl-1-piperazinyl]carbonyl]-2-phenyl]ethyl]amino]carbonyl]oxiranecarboxylic acid (0.36 g, 77.8%; Compound 11).

$^1$H NMR (CDCl$_3$) δ: 2.34–2.41 (m, 1H, piperazine ring), 2.82–2.96 (m, 2H, piperazine ring), 2.99–3.08 (m, 1H, piperazine ring), 3.06 (d, 2H, J=7.3 Hz, ph-CH$_2$—C—), 3.16–3.24 (m, 1H, piperazine ring), 3.49–3.58 (m, 1H, piperazine ring), 3.55 (d, 1H, J=1.7 Hz, epoxy ring), 3.57 (d, 1H, J=1.7 Hz, epoxy ring), 3.71 (t, 2H, J=5.1 Hz, piperazine ring), 4.5–6.0 (brd, 1H, —COOH), 5.23 (q, 1H, J=7.9 Hz, —N—CH—CO), 6.74–6.82 (m, 2H, aromatic), 6.91–7.00 (m, 2H, aromatic), 7.20–7.35 (m, 5H, aromatic), 8.23 (d, 1H, J=8.6 Hz, —NH—).

EXAMPLE 25

Using ethyl (2s,3s)-3-[[[[(1s)-1-[[4-(2-fluorophenyl)-1-piperazinyl]carbonyl]-2-phenyl]ethyl]amino]carbonyl]oxiranecarboxylate instead of ethyl (2s,3s)-3-[[[[(1s)-1-[[4-(4-fluorophenyl)-1-piperazinyl]-carbonyl]-2-phenyl]ethyl]amino]carbonyl]oxiranecarboxylate, the procedure of Example 24 was repeated to give (2s,3s)-3-[[[[(1s)-1-[[4-(2-fluorophenyl)-1-piperazinyl]carbonyl]-2-phenyl]ethyl]amino]carbonyl]oxiranecarboxylic acid (0.1 g, 29.6%; Compound 12).

$^1$H NMR (CDCl$_3$) δ: 2.38–2.43 (m, 1H, piperazine ring), 2.83–2.93 (m, 2H, piperazine ring), 2.95–3.08 (m, 1H, piperazine ring), 3.06 (d, 2H, J=7.6 Hz, ph-CH$_2$—C—), 3.20–3.28 (m, 1H, piperazine ring), 3.49–3.66 (m, 1H, piperazine ring), 3.55 (d, 1H, J=1.7 Hz, epoxy ring), 3.58 (d, 1H, J=1.3 Hz, epoxy ring), 3.67–3.80 (m, 2H, piperazine ring), 4.0–6.0 (brd, 1H, —COOH), 5.23 (q, 1H, J=7.9 Hz, —N—CH—CO), 6.77–6.87 (m, 1H, aromatic), 6.93–7.09 (m, 3H, aromatic), 7.20–7.36 (m, 5H, aromatic), 8.23 (d, 1H, J=8.6 Hz, —NH—).

EXAMPLE 26

Using ethyl (2s,3s)-3-[[[[(1s)-1-[[4-(4-fluorophenyl)-1-piperazinyl]carbonyl]-3-methyl]butyl]amino]carbonyl]oxiranecarboxylate instead of ethyl (2s,3s)-3-[[[[(1s)-1-[[4-(4-fluorophenyl)-1-piperazinyl]carbonyl]-2-phenyl]ethyl]

amino]carbonyl]oxiranecarboxylate, the procedure of Example 24 was repeated to give (2s,3s)-3-[[[[(1s)-1-[[4-(4-fluorophenyl-1-piperazinyl]carbonyl]-3-methyl]butyl]amino]carbonyl]oxiranecarboxylic acid (0.13 g, 69.5%; Compound 13).

$^1$H NMR (CDCl$_3$) δ: 0.96 (d, 3H, J=6.6 Hz, —C—CH$_3$), 0.99 (d, 3H, J=6.59 Hz, —C—CH$_3$), 1.42 (ddd, 1H, J=14.1, 10.5, 3.6 Hz, —C—CH$_2$—C), 1.6–1.82 (m, 1H, —C—CH—C$_2$), 1.69 (ddd, 1H, J=14.5, 10.7, 4.23 Hz, —C—CH$_2$—C), 3.08–3.26 (m, 4H, piperazine ring), 3.55 (d, 1H, J=1.7 Hz, epoxy ring), 3.60–3.92 (m, 4H, piperazine ring), 3.62 (d, 1H, J=1.8 Hz, epoxy ring), 5.08 (ddd, 1H, J=10.6, 8.6, 3.6 Hz, —N—CH—CO), 5.2–6.4 (brd, 1H, —COOH), 6.84–7.03 (m, 4H, aromatic), 8.18 (d, 1H, J=8.6 Hz, —NH—).

EXAMPLE 27

Using ethyl (2s,3s)-3-[[[[(1s)-1-[(4-phenyl-1-piperazinyl)carbonyl]-3-methyl]butyl]amino]carbonyl]oxiranecarboxylate instead of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 24 was repeated to give (2s,3s)-3-[[[[(1s)-1-[(4-phenyl-1-piperazinyl)carbonyl]-3-methyl]butyl]amino]carbonyl]oxiranecarboxylic acid (1.06 g, 29.1%; Compound 14).

$^1$H NMR (CDCl$_3$) δ: 0.96 (d, 3H, J=6.6 Hz, —C—CH$_3$), 0.99 (d, 3H, J=6.26 Hz, —C—CH$_3$), 1.37–1.47 (m, 1H, —C—CH—C$_2$), 1.64–1.80 (m, 2H, —C—CH$_2$—C—), 3.17–3.36 (m, 4H, piperazine ring), 3.55 (d, 1H, J=1.7 Hz, epoxy ring), 3.62 (d, 1H, J=1.3 Hz, epoxy ring), 3.70–3.90 (m, 4H, piperazine ring), 5.10 (m, 1H, —N—CH—CO), 6.5–7.5 (brd, 1H, —COOH), 6.87–6.96 (m, 3H, aromatic), 7.27–7.33 (m, 2H, aromatic), 8.20 (d, 1H, J=8.6 Hz, —NH—).

EXAMPLE 28

Using ethyl (2s,3s)-3-[[[[(1s)-1-[(4-dimethylsulfamoyl-1-piperazinyl)carbonyl]-3-methyl]butyl]amino]carbonyl]oxiranecarboxylate instead of ethyl (2s,3s)-3-[[[[(1s)-1-[[4-(4-fluorophenyl)-1-piperazinyl]carbonyl]-2-phenyl]ethyl]amino]carbonyl]oxirane carboxylate, the procedure of Example 24 was repeated to give (2s,3s)-3-[[[[(1s)-1-[(4-dimethylsulfamoyl-1-piperazinyl)carbonyl]-3-methyl]butyl]amino]carbonyl]oxiranecarboxylic acid (1.28 g, 39.0%; Compound 15).

$^1$H NMR (CDCl$_3$) δ: 0.94 (d, 3H, J=6.3 Hz, —C—CH$_3$), 0.96 (d, 3H, J=5.6 Hz, —C—CH$_3$), 1.36–1.44 (m, 1H, —C—CH—C$_2$), 1.61–1.68 (m, 2H, —C—CH$_2$—C—), 2.85 (s, 6H, —N—CH$_3$), 3.17–3.35 (m, 4H, piperazine ring), 3.48–3.60 (m, 2H, piperazine ring), 3.58 (d, 1H, J=1.7 Hz, epoxy ring), 3.62 (d, 1H, J=1.7 Hz, epoxy ring), 3.70–3.80 (m, 1H, piperazine ring), 3.83–3.95 (m, 1H, piperazine ring), 4.95–5.05 (m, 1H, —N—CH—CO), 7.7–8.1 (brd, 1H, —COOH), 7.94 (d, 1H, J=8.6 Hz, —NH—).

EXAMPLE 29

Using ethyl (2s,3s)-3-[[[[(1s)-1-[[4-(4-methylphenylsulfonyl)-1-piperazinyl]carbonyl]-3-methyl]-butyl]amino]carbonyl]oxiranecarboxylate instead of ethyl (2s,3s)-1-[[[[(1s)[[4-(4-fluorophenyl)-1-piperazinyl]carbonyl]-2-phenyl]ethyl]amino]carbonyl]oxiranecarboxylate, the procedure of Example 24 was repeated to give (2s,3s)-3-[[[[(1s)-1-[[4-(4-methylphenylsulfonyl)-1-piperazinyl]carbonyl]-3-methyl]butyl]amino]carbonyl]oxiranecarboxylic acid (2.8 g, 70.0%; Compound 16).

$^1$H NMR (CDCl$_3$) δ: 0.90 (d, 3H, J=6.6 Hz, —C—CH$_3$), 0.93 (d, 3H, J=6.6 Hz, —C—CH$_3$), 1.23–1.33 (m, 1H, —C—CH—C$_2$), 1.53–1.67 (m, 2H, —C—CH$_2$—C—), 2.45 (s, 3H, -ph-CH$_3$), 2.73–2.91 (m, 2H, piperazine ring), 3.28–3.59 (m, 4H, piperazine ring), 3.45 (d, 1H, J=1.7 Hz, epoxy ring), 3.48 (d, 1H, J=1.7 Hz, epoxy ring), 3.70–3.83 (m, 1H, piperazine ring), 3.98–4.08 (m, 1H, piperazine ring), 4.85–4.97 (m, 1H, —N—CH—CO), 7.35 (d, 2H, J=7.9 Hz, aromatic), 7.63 (d, 2H, J=8.3 Hz, aromatic), 7.97 (d, 1H, J=8.6 Hz, —NH—).

EXAMPLE 30

Using ethyl (2s,3s)-3-[[[[(1s)-1-[[4-(2-chlorophenyl)-1-piperazinyl]carbonyl]-3-methyl]butyl]amino]carbonyl]oxiranecarboxylate instead of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 24 was repeated to give (2s,3s)-3-[[[[(1s)-1-[[4-(2-chlorophenyl)-1-piperazinyl]carbonyl]-3-methyl]butyl]amino]carbonyl]oxiranecarboxylic acid (0.41 g, 67.2%; Compound 17).

$^1$H NMR (CDCl$_3$) δ: 0.97 (d, 3H, J=6.9 Hz, —C—CH$_3$), 0.98 (d, 3H, J=7.3 Hz, —C—CH$_3$), 1.38–1.47 (m, 1H, —C—CH—C$_2$), 1.65–1.77 (m, 2H, —C—CH$_2$—C—), 2.98–3.19 (m, 4H, piperazine ring), 3.55 (d, 1H, J=1.7 Hz, epoxy ring), 3.61–3.77 (m, 2H, piperazine ring), 3.64 (d, 1H, J=1.7 Hz, epoxy ring), 3.77–3.89 (m, 1H, piperazine ring), 3.89–4.15 (m, 1H, piperazine ring), 5.04–5.18 (m, 1H, —N—CH—CO), 7.00–7.06 (m, 2H, aromatic), 7.21–7.28 (m, 1H, aromatic), 7.37–7.41 (m, 1H, aromatic), 8.25 (d, 1H, J=8.9 Hz, —NH—).

EXAMPLE 31

Using ethyl (2s,3s)-3-[[[[(1s)-1-[[4-(3-chlorophenyl)-1-piperazinyl]carbonyl]-3-methyl]butyl]amino]carbonyl]oxiranecarboxylate instead of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 24 was repeated to give (2s,3s)-3-[[[[(1s)-1-[[4-(3-chlorophenyl)-1-piperazinyl]carbonyl]-3-methyl]butyl]amino]carbonyl]oxiranecarboxylic acid (0.39 g, 67.2%; Compound 18).

$^1$H NMR (CDCl$_3$) δ: 0.96 (d, 3H, J=6.6 Hz, —C—CH$_3$), 0.99 (d, 3H, J=6.6 Hz, —C—CH$_3$), 1.36–1.47 (m, 1H, —C—CH—C$_2$), 1.64–1.80 (m, 2H, —C—CH2—C—), 3.18–3.36 (m, 4H, piperazine ring), 3.53 (d, 1H, J=1.7 Hz, epoxy ring), 3.60–3.92 (m, 4H, piperazine ring), 3.62 (d, 1H, J=1.7 Hz, epoxy ring), 5.04–5.12 (m, 1H, —N—CH—CO), 5.5–6.5 (brd, 1H, —COOH), 6.77–6.82 (m, 1H, aromatic), 6.88–6.90 (m, 2H, aromatic), 7.17–7.23 (m, 1H, aromatic), 8.21 (d, 1H, J=8.6 Hz, —NH—).

EXAMPLE 32

Using ethyl (2s,3s)-3-[[[[(1s)-1-[[4-(4-chlorophenyl)-1-piperazinyl]carbonyl]-3-methyl]butyl]amino]carbonyl]oxiranecarboxylate instead of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 24 was repeated to give (2s,3s)-3-[[[[(1s)-1-[[4-(4-chlorophenyl)-1-piperazinyl]carbonyl]-3-methyl]butyl]amino]carbonyl]oxiranecarboxylic acid (0.33 g, 63.4%; Compound 19).

$^1$H NMR (CDCl$_3$) δ: 0.96 (d, 3H, J=6.6 Hz, —C—CH$_3$), 0.99 (d, 3H, J=6.59 Hz, —C—CH$_3$), 1.36–1.47 (m, 1H,

—C—CH—C$_2$), 1.64–1.80 (m, 2H, —C—CH$_2$—C—), 3.10–3.31 (m, 4H, piperazine ring), 3.54 (d, 1H, J=1.7 Hz, epoxy ring), 3.58–3.93 (m, 4H, piperazine ring), 3.62 (d, 1H, J=1.7 Hz, epoxy ring), 5.04–5.12 (m, 1H, —N—CH—CO), 4.8–6.5 (brd, 1H, —COOH), 6.82–6.88 (m, 2H, aromatic), 7.21–7.26 (m, 1H, aromatic), 8.18 (d, 1H, J=8.9 Hz, —NH—).

EXAMPLE 33

Using ethyl (2s,3s)-3-[[[[(1s)-1-[[4-(4-methoxyphenyl)-1-piperazinyl]carbonyl]-3-methyl]butyl]amino]carbonyl] oxiranecarboxylate instead of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 24 was repeated to give (2s,3s)-3-[[[[(1s)-1-[[4-(4-methoxyphenyl)-1-piperazinyl]carbonyl]-3-methyl]butyl]amino]carbonyl]oxiranecarboxylic acid (0.49 g, 56.7%; Compound 20).

$^1$H NMR (CDCl$_3$) δ: 0.95 (d, 3H, J=6.3 Hz, —C—CH$_3$), 0.99 (d, 3H, J=6.6 Hz, —C—CH$_3$), 1.38–1.46 (m, 1H, —C—CH—C$_2$), 1.63–1.80 (m, 2H, —C—CH$_2$—C—), 3.05–3.19 (m, 4H, piperazine ring), 3.55 (d, 1H, J=1.7 Hz, epoxy ring), 3.60–3.90 (m, 4H, piperazine ring), 3.62 (d, 1H, J=1.7 Hz, epoxy ring), 5.06–5.13 (m, 1H, —N—CH—CO), 4.8–5.8 (brd, 1H, —COOH), 6.84–7.00, (m, 4H, aromatic), 8.14 (d, 1H, J=8.6 Hz, —NH—).

EXAMPLE 34

Using ethyl (2s,3s)-3-[[[[(1s)-1-[[4-(2-chlorophenyl)-1-piperazinyl]carbonyl]-2-methyl]propyl]amino]carbonyl] oxiranecarboxylate instead of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 24 was repeated to give (2s,3s)-3-[[[[(1s)-1-[[4-(2-chlorophenyl)-1-piperazinyl]carbonyl]-2-methyl]propyl]amino]carbonyl]oxiranecarboxylic acid (1.09 g, 89.5%; Compound 21) as colorless crystals.

$^1$H NMR (CDCl$_3$) δ: 0.98 (d,3H, J=6.6 Hz, —C—CH$_3$), 1.01 (d, 3H, J=6.6 Hz, —C—CH$_3$, 2.10 (m, 1H, —CH—C$_2$), 2.98–3.14 (m, 4H, piperazine ring), 3.64 (d, J=1.6 Hz, 1H, epoxy ring), 3.66 (d, 1H, J=1.6 Hz, epoxy ring), 3.68–4.01 (m, 4H, piperazine ring), 4.98 (dd, 1H, J=8.9, 5.9 Hz, —N—CH—CO), 7.00–7.06 (m, 2H, aromatic), 7.24 (m, 1H, aromatic), 7.39 (m, 1H, aromatic), 8.29 (d, 1H, J=8.9, —NH).

EXAMPLE 35

Using ethyl (2s,3s)-3-[[[[[4-(2-chlorophenyl)-1-piperazinyl]carbonyl]methyl]amino]carbonyl] oxiranecarboxylate instead of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 24 was repeated to give (2s,3s)-3-[[[[4-(2-chlorophenyl)-1-piperazinyl]carbonyl]methyl]amino]carbonyl]oxiranecarboxylic acid (1.08 g, 66.5%; Compound 22) as colorless crystals.

$^1$H NMR (CDCl$_3$) δ: 3.02–3.09 (m, 4H, piperazine ring), 3.63 (m, 2H, piperazine ring), 3.66 (d, 1H, J=1.6 Hz, epoxy ring), 3.78 (d, 1H, J=1.6 Hz, epoxy ring), 3.80 (m, 2H, piperazine ring), 4.11 (dd, 1H, J=17.0, 5.4 Hz, —N—CH—CO), 4.33 (dd, 1H, J=17.0, 5.4 Hz, —N—CH—CO), 6.99–7.05 (m, 2H, aromatic), 7.23 (m, 1H, aromatic), 7.38 (m, 1H, aromatic), 8.67 (brd, 1H, —NH).

EXAMPLE 36

Using ethyl (2s,3s)-3-[[[(1s)-1-[[4-(2-chlorophenyl)-1-piperazinyl]carbonyl]ethyl]amino]carbonyl] oxiranecarboxylate instead of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 24 was repeated to give (2s,3s)-3-[[[(1s)-1-[[4-(2-chlorophenyl)-1-piperazinyl]carbonyl]ethyl]amino] carbonyl]oxiranecarboxylic acid (0.87 g, 77.5%; Compound 23) as colorless crystals.

$^1$H NMR (CDCl$_3$) δ: 1.41 (d, 3H, J=6.8 Hz, —C—CH3), 2.98–3.13 (m, 4H, piperazine ring), 3.61 (d, 1H, J=1.6 Hz, epoxy ring), 3.63 (d, 1H, J=1.6 Hz, epoxy ring), 3.67–3.84 (m, 3H, piperazine ring), 3.95 (m, 1H, piperazine ring), 5.06 (dq, 1H, J=8.4, 6.8 Hz, —N—CH—CO), 7.00–7.06 (m, 2H, aromatic), 7.24 (m, 1H, aromatic), 7.39 (m, 1H, aromatic), 8.13 (d, 1H, J=8.4, —NH).

EXAMPLE 37

Using ethyl (2s,3s)-3-[[[[(1s)-1-[[4-(2-chlorophenyl)-1-piperazinyl]carbonyl]-2-methyl]butyl]amino]carbonyl] oxiranecarboxylate instead of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 24 was repeated to give (2s,3s)-3-[[[[(1s)-1-[[4-(2-chlorophenyl)-1-piperazinyl]carbonyl]-2-methyl]butyl]amino]carbonyl]oxiranecarboxylic acid (1.07 g, 77.4%; Compound 24) as colorless crystals.

$^1$H NMR (CDCl$_3$) δ: 0.92 (t, 3H, J=7.3 Hz, —C—CH$_3$), 1.00 (d, 3H, J=6.8 Hz, —C—CH$_3$), 1.22 (m, 1H, —CH—C$_2$—), 1.54 (m, 1H, —CH—C), 1.84 (m, 1H, —CH—C), 2.97–3.17 (m, 4H, piperazine ring), 3.60 (d, 1H, J=1.6 Hz, epoxy ring), 3.64 (d, 1H, J=1.6 Hz, epoxy ring), 3.65–3.79 (m, 2H, piperazine ring), 3.85–4.05 (m, 2H, piperazine ring), 4.98 (dd, 1H, J=9.2, 6.3 Hz, —N—CH—CO), 7.00–7.06 (m, 2H, aromatic), 7.24 (m, 1H, aromatic), 7.39 (m, 1H, aromatic), 8.29 (d, 1H, J=9.2, —NH).

EXAMPLE 38

Using ethyl (2s,3s)-3-[[[2-[[4-(2-chlorophenyl)-1-piperazinyl]carbonyl]ethyl]amino]carbonyl] oxiranecarboxylate instead of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 24 was repeated to give (2s,3s)-3-[[[2-[[4-(2-chlorophenyl)-1-piperazinyl]carbonyl]ethyl]amino] carbonyl]oxiranecarboxylic acid (0.85 g, 78.9%; Compound 25) as colorless crystals.

$^1$H NMR (DMSO-d$_6$) δ: 2.56 (t, 2H, J=6.9 Hz, —C—CH$_2$—CO), 2.91–2.98 (m, 4H, piperazine ring), 3.35 (td, 2H, J=6.9, 5.6 Hz, —N—CH$_2$—C), 3.49 (d, 1H, J=2.0 Hz, epoxy ring), 3.59 (d, 1H, J=1.6 Hz, epoxy ring), 3.56–3.64 (m, 2H, piperazine ring), 3.80 (m, 2H, piperazine ring), 7.07 (td, 1H, J=7.9, 1.7 Hz, aromatic), 7.15 (dd, 1H, J=7.9, 1.7 Hz, aromatic), 7.43 (dd, 1H, J=7.9, 1.7 Hz, aromatic), 7.31 (m, 1H, aromatic), 8.40 (t, 1H, J=5.6 Hz, —NH), 13.50 (brd, 1H, —COOH).

EXAMPLE 39

Using ethyl (2s,3s)-3-[[[[N-[[4-(2-chlorophenyl)-1-piperazinyl]carbonyl]methyl]-N-methyl]amino]carbonyl] oxiranecarboxylate instead of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 24 was repeated to give (2s,3s)-3-[[[[N-[[4-(2-chlorophenyl)-1-piperazinyl]carbonyl]methyl]-N-methyl]amino]carbonyl]oxiranecarboxylic acid (1.08 g, 74.8,; Compound 26) as colorless crystals.

¹H NMR (CDCl₃) δ : 3.01–3.10 (m, 6H, piperazine ring), 3.27 (s, 3H, —NCH₃), 3.63–3.71 (m, 2H, —N—CH₂—CO), 3.75 (d, 1H, J=1.9 Hz, epoxy ring), 3.78–3.90 (m, 2H, piperazine ring), 4.02 (d, 1H, J=1.9 Hz, epoxy ring), 6.98–7.05 (m, 2H, aromatic), 7.24 (m, 1H, aromatic), 7.36 (m, 1H, aromatic).

EXAMPLE 40

Using ethyl (2s,3s)-3-[[(2s)-2-[[4-(2-chlorophenyl)-1-piperazinyl]carbonyl]-1-pyrrolidinyl]carbonyl]-oxiranecarboxylate instead of ethyl (2s,3s)-3-[[[[(1s)-1-[[4-(4-fluorophenyl)1-piperazinyl]carbonyl]-2-phenyl]ethyl]amino]carbonyl]oxiranecarboxylate, the procedure of Example 24 was repeated to give (2s,3s)-3-[[(2s)-2-[[4-(2-chloro-phenyl)-1-piperazinyl]carbonyl]-1-pyrrolidinyl]carbonyl]oxiranecarboxylic acid (0.94 g, 7.07%; Compound 27) as colorless crystals.

¹H NMR (CDCl₃) δ: 1.94–2.11 (m, 2H, pyrrolidine ring), 2.17–2.30 (m, 2H, pyrrolidine ring), 3.06–3.20 (m, 4H, piperazine ring), 3.63–3.76 (m, 2H, piperazine ring), 3.81–3.85 (m, 5H), 4.00 (dt, 1H, J=13.7, 4.4 Hz, pyrrolidine ring), 4.96 (dd, 1H, J=7.8, 4.3 Hz, pyrrolidine ring), 6.97–7.04 (m, 2H, aromatic), 7.24 (m, 1H, aromatic), 7.37 (m, 1H, aromatic).

EXAMPLE 41

Using ethyl (2s,3s)-3-[[[[(1s)-1-[[4-(2-chlorophenyl)-1-piperazinyl]carbonyl]-2-acetylaminomethylthio]ethyl]amino]carbonyl]oxiranecarboxylate instead of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 24 was repeated to give (2s,3s)-3-[[[[(1s)1-[[4-(2-chlorophenyl)-1-piperazinyl]carbonyl]-2-acetylaminomethylthio]-ethyl]amino]carbonyl]oxiranecarboxylic acid (0.88 g, 77.9%; Compound 28) as colorless crystals.

¹H NMR (CDCl₃) δ: 2.05 (s, 3H, —COOH₃), 2.85 (dd, 1H, J=13.9, 8.3 Hz, —C—CH—S), 2.96–3.16 (m, 5H), 3.69 (d, 1H, J=1.6 Hz, epoxy ring), 3.78 (d, 1H, J=1.6 Hz, epoxy ring), 3.71–3.89 (m, 4H, piperazine ring), 4.39 (d, 2H, J=8.3 Hz, —S—CH₂—N), 5.21 (m, 1H, —N—CH—CO), 6.97–7.02 (m, 2H, aromatic), 7.22 (m, 1H, aromatic), 7.36 (m, 1H, aromatic), 7.80 (d, 1H, J=8.3, —NH), 9.00 (brd, 1H, —NH).

EXAMPLE 42

Using ethyl (2s,3s)-3-[[[[(1s)-1-[[4-(2-chlorophenyl)-1-piperazinyl]carbonyl]-3-methylthio]propyl]amino]carbonyl]oxiranecarboxylate instead of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 24 was repeated to give (2s,3s)-3-[[[[(1s)-1-[[4-(2-chlorophenyl)-1-piperazinyl]carbonyl]-3-methylthio]propyl]amino]carbonyl]oxiranecarboxylic acid (1.17 g, 80.7%; Compound 29) as colorless crystals.

¹H NMR (CDCl₃) δ: 1.98 (dd, 2H, J=6.9, 6.6 Hz, —CH—C—C), 2.12 (s, 3H, —SCH₃), 2.57 (dt, 2H, J=6.9, 2.3 Hz, —C—CH₂—C—S), 3.05–3.19 (m, 4H, piperazine ring), 3.63 (d, 1H, J=1.9 Hz, epoxy ring), 3.65 (d, 1H, J=1.9 Hz, epoxy ring), 3.71–3.94 (m, 4H, piperazine ring), 5.26 (m, 1H, —N—CH—CO), 7.00–7.06 (m, 2H, aromatic), 7.24 (m, 1H, aromatic), 7.38 (m, 1H, aromatic), 8.18 (d, 1H, J=8.6, —NH).

EXAMPLE 43

Using ethyl (2s,3s)-3-[[[[(1s)-1-[[4-(2-chlorophenyl)-1-piperazinyl]carbonyl]-3-carbamoyl]propyl]amino]carbonyl]oxiranecarboxylate instead of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 24 was repeated to give (2s,3s)-3-[[[[(1s)-1-[[4-(2-chlorophenyl)-1-piperazinyl]carbonyl]-3-carbamoyl]propyl]amino]carbonyl]oxiranecarboxylic acid (0.14 g, 74.5%; Compound 30) as colorless crystals.

¹H NMR (CDCl₃) δ: 1.85 (brd, 2H, —NH₂), 2.14 (m, 1H, 13 C—CH—C—CO—), 2.36–2.53 (m, 3H, —CH—CH₂—C—CO—), 2.89–3.06 (m, 4H, piperazine ring), 3.57–3.79 (m, 6H, piperazine and epoxy ring), 5.02 (m, 1H, —N—CH—CO), 6.96–7.02 (m, 2H, aromatic), 7.21 (m, 1H, aromatic), 7.37 (m, 1H, aromatic), 7.88 (brd, 1H, —NH).

EXAMPLE 44

Using ethyl (2s,3s)-3-[[[(1s)-1-[[4-(4-fluorophenyl)-1-piperazinyl]carbonyl]-1-cyclopentyl]amino]carbonyl]oxiranecarboxylate instead of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 24 was repeated to give (2s,3s)-3-[[[(1s)-1-[[4-(4-fluorophenyl)-1-piperazinyl]carbonyl]-1-cyclopentyl]amino]carbonyl]oxiranecarboxylic acid (0.52 g, 55.6%; Compound 31) as colorless crystals.

¹H NMR (DMSO-d₆) δ: 1.61 (m, 4H, cyclopentyl), 1.87 (m, 2H, cyclopentyl), 2.22 (m, 2H, cyclopentyl), 2.97 (m, 4H, piperazine), 3.45 (d, 1H, J=1.6 Hz, epoxy ring), 3.58 (d, 1H, J=2.1 Hz, epoxy ring), 3.60 (m, 4H, piperazine ring), 6.95–7.20 (m, 4H, aromatic), 8.89 (s, 1H, —NH), 13.4 (brd, 1H, —COOH).

EXAMPLE 45

To a solution of the (2s,3s)-3-[[[[(1s)-1-[[4-(4-methylphenylsulfonyl)-1-piperazinyl]carbonyl]-3-methyl]butyl]amino]carbonyl]oxiranecarboxylic acid (0.935 g, 2 mmol) obtained in Example 29 in dichloromethane (15 ml) were added o-benzylhydroxylamine (0.638 g, 4.0 mmol) and N-methylmorpholine (0.405 g, 4.0 mmol). Then, a solution of dicyclohexylcarbodiimide (0.619 g, 3.0 mmol) in dichloromethane (5 ml) was added dropwise under ice-cooling. The mixture was stirred at room temperature for 24 hours, at the end of which time it was filtered. The precipitate was washed with dichloromethane (20 ml) and the washing and the filtrate were pooled and washed with water. The organic layer was dried over anhydrous magnesium sulfate and concentrated under reduced pressure and the residue was chromatographed on silica gel. Elution was carried out with ethyl acetate-hexane (2:1, v/v) to provide (2s,3s)-3-[[[[(1s)-1-[[4-(4-methylphenylsulfonyl)-1-piperazinyl]carbonyl]-3-methyl]butyl]amino]carbonyl]oxiranecarbobenzyloxamide (0.86 g, 75.1%; Compound 32).

¹H NMR (CDCl₃) δ: 0.84 (d, 3H, J=6.2 Hz, —C—CH₃), 0.91 (d, 3H, J=6.5 Hz, —C—CH₃), 1.23–1.31 (m, 1H, —C—CH₂—C), 1.36–1.58 (m, 2H, —C—CH—C, —C—CH—C₂), 2.43 (s, 3H, -ph-CH₃), 2.72–2.86 (m, 2H, piperazine ring), 3.14–3.27 (m, 2H, piperazine ring), 3.31–3.51 (m, 2H, piperazine ring), 3.40 (d, 1H, J=1.4 Hz, epoxy ring), 3.43 (d, 1H, J=1.7 Hz, epoxy ring), 3.63–3.74 (m, 1H, piperazine ring), 3.84–3.98 (m, 1H, piperazine ring), 4.80–4.90 (m, 1H, —N—CH—CO), 4.87 (s, 3H, —O—CH2-ph), 7.30–7.40 (m, 8H, aromatic, —NH—), 7.56–7.66 (m, 2H, aromatic), 9.05 (s, 1H, —NH—).

EXAMPLE 46

To a solution of the (2s,3s)-3-[[[[(1s)-1-[[4-(4-methylphenylsulfonyl)-1-piperazinyl]carbonyl]-3-methyl]

butyl]amino]carbonyl]oxiranecarbobenzyloxamide (0.57 g, 1 mmol) obtained in Example 45 in methanol (25 ml) was added a catalyst amount of palladium-on-carbon and catalytic reduction was carried out. After completion of the reaction, the palladium-on-carbon was filtered off and the filtrate was concentrated and chromatographed on silica gel. Elution was carried out with ethyl acetate to provide (2s, 3s)-3-[[[[(1s)-1-[[4-(4-methylphenylsulfonyl)-1-piperazinyl]carbonyl]-3-methyl]butyl]amino]carbonyl]oxiranecarbohydroxamic acid (0.18 g, 37.3%; Compound 33).

$^1$H NMR (CDCl$_3$) δ: 0.84 (d, 3H, J=5.9 Hz, —C—CH$_3$), 0.90 (d, 3H, J=5.9 Hz, —C—CH$_3$), 1.24–1.33 (m, 1H, —C—CH$_2$—C), 1.50–1.64 (m, 2H, —C—CH—C, —C—CH—C$_2$), 2.42 (s, 3H, -ph-CH$_3$), 2.90–3.20 (m, 4H, piperazine ring), 3.44–3.80 (m, 3H, piperazine ring), 3.51 (s, 1H, epoxy ring), 3.68 (s, 1H, epoxy ring), 4.56–4.66 (m, 1H, piperazine ring), 4.76–4.90 (m, 1H, —N—CH—CO), 7.33 (d, 2H, J=7.8 Hz, aromatic), 7.62 (dd, 2H, J=7.8, 1.7 Hz, aromatic), 7.84–7.94 (brd, 1H, —NH—), 9.80–10.40 (brd, 1H, —OH).

EXAMPLE 47

| Tablets: | |
|---|---|
| Compound 23 | 80 mg |
| Starch | 17 mg |
| Magnesium stearate | 3 mg |

The above components per tablet are compressed into tablets in the routine manner. Where necessary, the tablets can be sugar-coated.

EXAMPLE 48

| Capsules | |
|---|---|
| Compound 18 | 50 mg |
| Lactose | 100 mg |
| Starch | 30 mg |
| Magnesium stearate | 10 mg |

The above components per tablet are mixed and filled in gelatin capsule shells.

EXAMPLE 49

| Injection | |
|---|---|
| Compound 21 | 2.5 mg |
| Sodium chloride | 900 mg |
| 1N-sodium hydroxide | q.s. |
| Distilled water for injection | to make 100 ml |

Distilled water for injection to make 100 ml

The above components are mixed in the routine manner to provide an injection.

EXAMPLE 50

| Ophthalmic solution | |
|---|---|
| Compound 18 | 50 mg |
| Boric acid | 700 mg |
| Borax | q.s. |
| Sodium chloride | 500 mg |
| Sodium edetate | 0.05 mg |
| Benzalkonium chloride | 0.005 mg |
| Sterilized pure water | to make 100 ml |

The above components are mixed in the routine manner to provide an ophthalmic solution.

EXAMPLE 51

N-(2-Naphthalenesulfonyl)-L-valyl-L-leucinal

Valine (11.5 g) was dissolved in 1M aqueous sodium hydroxide solution (100 ml), and purified water (200 ml) and tetrahydrofuran (100 ml) were added. Thereto were simultaneously added dropwise 1M aqueous sodium hydroxide solution (100 ml) and a solution (100 ml) of 2-naphthalenesulfonyl chloride (18.5 g) in tetrahydrofuran with stirring under ice-cooling. The solution was stirred for one day at room temperature to allow reaction. After the completion of the reaction, the reaction mixture was adjusted to pH 2–3 and extracted with ethyl acetate. The extract was washed with dilute hydrochloric acid and saturated brine, and dried over anhydrous magnesium sulfate. Ethyl acetate was evaporated under reduced pressure, and the residue was washed with a mixture of hexane-ethyl acetate to give 12.8 g of N-(2-naphthalenesulfonyl)-L-valine as white crystals.

N-(2-Naphthalenesulfonyl)-L-valine (12.0 g) and N-hydroxysuccinimide (5.4 g) were dissolved in tetrahydrofuran (200 ml), and a solution (200 ml) of 1-ethyl-3-(3-dimethylaminopropyl)carbodiimide hydrochloride (9.0 g) in dichloromethane was gradually added dropwise with stirring under ice-cooling. The solution was stirred for 4 hr at room temperature to allow reaction. After the completion of the reaction, the solvent was evaporated under reduced pressure and the residue was dissolved in ethyl acetate. The mixture was washed with dilute hydrochloric acid, saturated aqueous solution of sodium hydrogen-carbonate and saturated brine, and dried over anhydrous magnesium sulfate. Ethyl acetate was evaporated under reduced pressure, and the residue was washed with a mixed solution of hexane-ethyl acetate to give 14.1 g of N-(2-naphthalenesulfonyl)-L-valine N-hydroxysuccinimide ester as white crystals.

N-(2-Naphthalenesulfonyl)-L-valine N-hydroxysuccinimide ester (1.8 g) and leucinol (0.63 g) were added to dichloromethane (100 ml), and the mixture was stirred at room temperature while adding triethylamine (0.68 g). The solution was stirred for 2 hr to allow reaction. After the completion of the reaction, the mixture was washed with dilute hydrochloric acid, saturated aqueous solution of sodium hydrogen-carbonate and saturated brine, and dried over anhydrous magnesium sulfate. Dichloromethane was evaporated under reduced pressure, and the residue was washed with a mixed solution of hexane-ethyl acetate to give 1.3 g of N-(2-naphthalenesulfonyl)-L-valyl-L-leucinol as white crystals.

N-(2-Naphthalenesulfonyl)-L-valyl-L-leucinol (1.3 g) was dissolved in dimethyl sulfoxide (20 ml) and dichloromethane (10 ml), and triethylamine (1.9 g) was added. The solution was stirred at room temperature while adding a solution (20 ml) of sulfur trioxide-pyridine complex (2.0 g) in dimethyl sulfoxide, which was followed by stirring for 2 hr. After the completion of the reaction, ethyl acetate was added. The mixture was washed with dilute hydrochloric acid, saturated aqueous solution of sodium hydrogencarbonate and saturated brine, and dried over anhydrous magnesium sulfate. The solvent was evaporated under reduced pressure, and the residue was washed with a mixed solution of hexane-ethyl acetate to give 0.98 g of N-(2-naphthalenesulfonyl)-L-valyl-L-leucinal (Compound 34) as white crystals. [Step 1]

$^1$H-NMR (DMSO-d$_6$ 270 MHz) δ: 0.42 (d, 3H, J=6.3 Hz), 0.55 (d, 3H, J=6.3 Hz), 0.84 (d, 3H, J=6.6 Hz), 0.88 (d, 3H, J=6.6 Hz), 0.93–1.12 (m, 2H), 1.14–1.28 (m, 1H), 1.82–2.00 (m, 1H), 3.63–3.72 (m, 2H), 7.62–8.40 (m, 9H), 9.02 (s, 1H).

Anal. ($C_{21}H_{28}N_2O_4S$) C, H, N.

In the same manner as in Step 1 except that 4-fluorobenzenesulfonyl chloride was used instead of 2-naphthalenesulfonyl chloride of Step 1, N-(4-fluorophenylsulfonyl)-L-valyl-L-leucinal (Compound 35) was obtained as white crystals. [Step 2]

$^1$H-NMR (DMSO-d$_6$ 270 MHz) δ: 0.74 (d, 3H, J=5.9 Hz), 0.80 (d, 6H, J=6.4 Hz), 0.85 (d, 3H, J=6.8 Hz), 1.14–1.46 (m, 3H), 1.81–1.93 (m, 1H), 3.56–3.62 (dd, 1H, J=6.6, 9.5 Hz), 3.80–3.88 (m, 1H), 7.33–7.42 (m, 2H), 7.79–7.86 (m, 2H), 7.96 (d, 1H, J=9.8 Hz), 8.27 (d, 1H, J=7.3 Hz), 9.14 (s, 1H).

Anal. ($C_{17}H_{25}FN_2O_4S$) C, H, N.

In the same manner as in Step 1 except that 4-chlorobenzenesulfonyl chloride was used instead of 2-naphthalenesulfonyl chloride of Step 1, N-(4-chlorophenylsulfonyl)-L-valyl-L-leucinal (Compound 36) was obtained as white crystals. [Step 3]

$^1$H-NMR (DMSO-d$_6$ 270 MHz) δ: 0.74 (d, 3H, J=5.9 Hz), 0.82 (d, 6H, J=6.8 Hz), 0.88 (d, 3H, J=6.3 Hz), 1.15–1.46 (m, 1H), 3.61 (dd, 1H, J=6.8, 9.3 Hz), 3.82–3.90 (m, 1H), 7.56–7.63 (m, 2H), 7.44–7.79 (m, 2H), 8.03 (d, 1H, J=9.3 Hz), 8.26 (d, 1H, J=7.3 Hz), 9.15 (s, 1H).

Anal. ($C_{17}H_{25}ClN_2O_4S$) C, H, N.

In the same manner as in Step 1 except that p-toluenesulfonyl chloride was used instead of 2-naphthalenesulfonyl chloride of Step 1, N-(4-methylphenylsulfonyl)-L-valyl-L-leucinal (Compound 37) was obtained as white crystals. [Step 4]

$^1$H-NMR (DMSO-d$_6$ 270 MHz) δ: 0.72–0.90 (m, 12H), 1.18–1.45 (m, 3H), 1.79–1.91 (m, 1H), 2.36 (s, 3H), 3.57 (t, 1H, J=7.7 Hz), 3.77–3.84 (m, 1H), 7.32 (d, 2H), 7.62–7.70 (m, 2H), 7.76 (d, 1H, J=8.3 Hz), 8.26 (d, 1H, J=6.8 Hz), 9.07 (s, 1H).

Anal. ($C_{18}H_{28}N_2O_4S$) C, H, N.

In the same manner as in Step 1 except that tert-leucine was used instead of valine of Step 1, N-(2-naphthalenesulfonyl)-L-tert-leucyl-L-leucinal (Compound 38) was obtained as white crystals. [Step 5]

$^1$H-NMR (DMSO-d$_6$ 270 MHz) δ: 0.35 (d, 3H, J=6.4 Hz), 0.46 (d, 3H, J=6.4 Hz), 0.78–0.95 (m, 2H), 0.95 (s, 9H), 1.08–1.20 (m, 1H), 3.45–3.55 (m, 1H), 3.67 (d, 1H, J=10.3 Hz), 7.62–7.72 (m, 2H), 7.82–7.86 (m, 1H), 7.97–8.10 (m, 4H), 8.17 (d, 1H, J=6.4 Hz), 8.29 (m, 1H), 8.91 (s, 1H).

Anal. ($C_{22}H_{30}N_2O_4S$) C, H, N.

In the same manner as in Step 1 except that 4-fluorobenzenesulfonyl chloride was used instead of 2-naphthalenesulfonyl chloride, and D-valine was used instead of valine of Step 1, N-(4-fluorophenylsulfonyl)-D-valyl-L-leucinal (Compound 39) was obtained as white crystals. [Step 6]

$^1$H-NMR (DMSO-d$_6$ 270 MHz) δ: 0.78 (d, 3H, J=6.3 Hz), 0.82 (d, 3H, J=6.9 Hz), 0.83 (d, 6H, J=6.3 Hz), 1.24–1.50 (m, 3H), 1.80–1.92 (m, 1H), 3.62 (s br, 1H), 3.84–3.92 (m, 1H), 7.32–7.41 (m, 2H), 7.79 (m, 3H), 8.33 (d, 1H, J=6.9 Hz), 8.96 (s, 1H).

Anal. ($C_{22}H_{30}N_2O_4S$) C, H, N.

In the same manner as in Step 1 except that 4-fluorobenzenesulfonyl chloride was used instead of 2-naphthalenesulfonyl chloride, and norleucine was used instead of valine of Step 1, N-(4-fluorophenylsulfonyl)-L-norleucyl-L-leucinal (Compound 40) was obtained as white crystals. [Step 7]

$^1$H-NMR (DMSO-d$_6$ 270 MHz) δ: 0.74–0.90 (m, 9H), 1.07–1.59 (m, 9H), 3.76 (t, 1H, J=5.4 Hz), 3.84–3.91 (m, 1H), 7.34–7.45 (m, 2H), 7.79–8.07 (m, 3H), 8.29 (d, 1H, J=7.3 Hz), 9.18 (s, 1H).

Anal. ($C_{22}H_{30}N_2O_4S$) C, H, N.

In the same manner as in Step 1 except that 4-fluorobenzenesulfonyl chloride was used instead of 2-naphthalenesulfonyl chloride, and norvaline was used instead of valine of Step 1, N-(4-fluorophenylsulfonyl)-L-norvalyl-L-leucinal (Compound 41) was obtained as white crystals. [Step 8]

$^1$H-NMR (DMSO-d$_6$ 270 MHz) δ: 0.69–0.85 (m, 9H), 1.14–1.66 (m, 7H), 3.78 (t, 1H, J=6.3 Hz), 3.84–3.92 (m, 1H), 7.34–7.42 (m, 2H), 7.79–8.02 (m, 3H), 8.28 (d, 1H, J=7.3 Hz), 9.18 (s, 1H).

Anal. ($C_{22}H_{30}N_2O_4S$) C, H, N.

EXAMPLE 52

N-(2-Naphthalenesulfonyl)-L-tert-leucyl-L-phenylalaninal tert-Leucine (13.1 g) was dissolved in 1M aqueous sodium hydroxide solution (100 ml), and purified water (200 ml) and tetrahydrofuran (100 ml) were added. Thereto were simultaneously added dropwise 1M aqueous sodium hydroxide solution (100 ml) and a solution (100 ml) of 2-naphthalenesulfonyl chloride (20.4 g) in tetrahydrofuran with stirring under ice-cooling. The solution was stirred for one day at room temperature to allow reaction. After the completion of the reaction, the reaction mixture was adjusted to pH 2–3 and extracted with ethyl acetate. The extract was washed with dilute hydrochloric acid and saturated brine, and dried over anhydrous magnesium sulfate. Ethyl acetate was evaporated under reduced pressure, and the residue was washed with a mixture of hexane-ethyl acetate to give 16.5 g of N-(2-naphthalenesulfonyl)-L-tert-leucine as white crystals.

N-(2-Naphthalenesulfonyl)-L-tert-leucine (16.0 g) and N-hydroxysuccinimide (6.9 g) were dissolved in tetrahydrofuran (200 ml), and a solution (200 ml) of 1-ethyl-3-(3-dimethylaminopropyl)carbodiimide hydrochloride (11.5 g) in dichloromethane was gradually added dropwise with stirring under ice-cooling. The solution was stirred at room temperature for about 12 hr to allow reaction. After the completion of the reaction, the solvent was evaporated under reduced pressure and the residue was dissolved in ethyl acetate. The mixture was washed with dilute hydrochloric acid, saturated aqueous solution of sodium hydrogencarbonate and saturated brine, and dried over anhydrous magnesium sulfate. Ethyl acetate was evaporated under reduced pressure, and the residue was washed with a mixed solution of hexane-ethyl acetate to give 18.3 g of N-(2-naphthalenesulfonyl)-L-tert-leucine N-hydroxysuccinimide ester as white crystals.

N-(2-Naphthalenesulfonyl)-L-tert-leucine N-hydroxysuccinimide ester (1.8 g) and phenylalaninol (1.0 g) were added to dichloromethane (50 ml), and the mixture was stirred at room temperature while adding triethylamine (0.86 g). The solution was stirred for 2 hr to allow reaction. After the completion of the reaction, the mixture was washed with dilute hydrochloric acid, saturated aqueous solution of sodium hydrogencarbonate and saturated brine, and dried over anhydrous magnesium sulfate. Dichloromethane was evaporated under reduced pressure, and the residue was washed with a mixed solution of hexane-ethyl acetate to give 1.6 g of N-(2-naphthalenesulfonyl)-L-tert-leucyl-L-phenylalaninol as white crystals.

N-(2-Naphthalenesulfonyl)-L-tert-leucyl-L-phenylalaninol (1.6 g) was dissolved in dimethyl sulfoxide (20 ml) and dichloromethane (10 ml), and triethylamine (2.1 g) was added. The solution was stirred at room temperature while adding a solution (15 ml) of sulfur trioxide-pyridine complex (2.2 g) in dimethyl sulfoxide, which was followed by stirring for 2 hr. After the completion of the reaction, ethyl acetate was added. The mixture was washed with dilute hydrochloric acid, saturated aqueous solution of sodium hydrogencarbonate and saturated brine, and dried over anhydrous magnesium sulfate. The solvent was evaporated under reduced pressure, and the residue was washed with a mixed solution of hexane-ethyl acetate to give 1.1 g of N-(2-naphthalenesulfonyl)-L-tert-leucyl-L-phenylalaninal (Compound 42) as white crystals. [Step 1]

$^1$H-NMR (DMSO-$d_6$ 270 MHz) δ: 0.86 (s, 9H), 2.26–2.40 (m, 1H), 2.63–2.77 (m, 1H), 3.56 (dd, 1H, J=6.8, 13.2 Hz), 3.63–3.68 (m, 1H), 6.87–6.90 (m, 1H), 6.99–7.03 (m, 1H), 7.11–7.22 (m, 3H), 7.60–7.72 (m, 2H), 7.80–7.87 (m, 1H), 7.92–8.19 (m, 4H), 8.35 (d, 1H, J=6.8 Hz), 8.40–8.43 (m, 1H), 8.63 (s, 1H).

Anal. ($C_{25}H_{28}N_2O_4S$) C, H, N.

In the same manner as in Step 1 except that 4-fluorobenzenesulfonyl chloride was used instead of 2-naphthalenesulfonyl chloride, and valine was used instead of tert-leucine of Step 1, N-(4-fluorophenylsulfonyl)-L-valyl-L-phenylalaninal (Compound 43) was obtained as white crystals. [Step 2]

$^1$H-NMR (DMSO-$d_6$ 270 MHz) δ: 0.76 (d, 3H, J=6.4 Hz), 0.77 (d, 3H, J=6.4 Hz), 1.69–1.86 (m, 1H), 2.67 (dd, 1H, J=8.8, 14.2 Hz), 3.02 (dd, 1H, J=5.1, 14.2 Hz), 3.56 (dd, 1H, J=6.4, 9.3 Hz), 3.99–4.07 (m, 1H), 7.12–7.29 (m, 7H), 7.72–7.84 (m, 2H), 7.92 (d, 1H, J=9.3 Hz), 8.44 (d, 1H, J=6.8 Hz), 9.07 (s, 1H).

Anal. ($C_{20}H_{23}FN_2O_4S$) C, H, N.

In the same manner as in Step 1 except that valine was used instead of tert-leucine of Step 1, N-(2-naphthalenesulfonyl)-L-valyl-L-phenylalaninal (Compound 44) was obtained as white crystals. [Step 3]

$^1$H-NMR (DMSO-$d_6$ 270 MHz) δ: 0.63 (d, 3H, J=6.6 Hz), 0.76 (d, 3H, J=6.6 Hz), 1.68–1.82 (m, 1H,), 2.40–2.92 (m, 1H), 3.64 (dd, 1H, J=6.6, 9.2 Hz), 3.97–3.87 (m, 1H), 6.95–7.02 (m, 2H), 7.10–7.23 (m, 3H), 7.62–7.82 (m, 3H), 7.94–8.10 (m, 4H), 8.36–8.43 (m, 2H), 8.86 (s, 1H).

Anal. ($C_{24}H_{26}N_2O_4S$) C, H, N.

In the same manner as in Step 1 except that 4-chlorobenzenesulfonyl chloride was used instead of 2-naphthalenesulfonyl chloride, and valine was used instead of tert-leucine of Step 1, N-(4-chlorophenylsulfonyl)-L-valyl-L-phenylalaninal (Compound 45) was obtained as white crystals. [Step 4]

$^1$H-NMR (DMSO-$d_6$ 270 MHz) δ: 0.77 (d, 3H, J=6.8 Hz), 0.79 (d, 3H, J=6.8 Hz), 1.70–1.87 (m, 1H), 2.67 (dd, 1H, J=8.8, 14.2 Hz), 3.01 (dd, 1H, J=5.4, 14.2 Hz), 3.60 (dd, 1H, J=6.4, 9.3 Hz), 4.00–4.07 (m, 1H), 7.12–7.32 (m, 5H), 7.50–7.60 (m, 2H), 7.68–8.00 (m, 2H), 7.98 (d, 1H, J=9.3 Hz), 8.44 (d, 1H, J=6.8 Hz), 9.09 (s, 1H).

Anal. ($C_{20}H_{23}ClN_2O_4S$) C, H, N.

In the same manner as in Step 1 except that p-toluenesulfonyl chloride was used instead of 2-naphthalenesulfonyl chloride, and valine was used instead of tert-leucine of Step 1, N-(4-methylphenylsulfonyl)-L-valyl-L-phenylalaninal (Compound 46) was obtained as white crystals. [Step 5]

$^1$H-NMR (DMSO-$d_6$ 270 MHz) δ: 0.74 (d, 6H, J=6.4 Hz), 1.71–1.81 (m, 1H), 2.33 (s, 3H), 2.65 (dd, 1H, J=8.8, 14.2), 2.99 (dd, 1H, J=5.4, 14.2), 3.55 (dd, 1H, J=6.4, 9.3 Hz), 3.97–4.05 (m, 1H), 7.11–7.37 (m, 7H), 7.59–7.66 (m, 2H), 7.73 (d, 1H, J=9.3 Hz), 8.41 (d, 1H, J=6.8 Hz), 8.99 (s, 1H).

Anal. ($C_{21}H_{26}N_2O_4S$) C, H, N.

In the same manner as in Step 1 except that 1-aminocyclohexanecarboxylic acid was used instead of tert-leucine of Step 1, 1-(2-naphthalenesulfonylamino) cyclohexanecarbonyl-L-phenylalaninol (Compound 47) was obtained as white crystals. [Step 6]

$^1$H-NMR (DMSO-$d_6$ 270 MHz) δ: 1.12 (s br, 6H), 1.65 (s br, 4H), 2.28 (dd, 1H, J=8.6, 14.2 Hz), 3.06 (dd, 1H, J=5.3, 14.2 Hz), 4.07–4.14 (m, 1H), 7.16–7.29 (m, 5H), 7.63–7.72 (m, 2H), 7.86–7.72 (m, 2H), 7.98–8.15 (m, 4H), 8.41 (s, 1H), 9.29 (s, 1H).

Anal. ($C_{26}H_{28}N_2O_4S$) C, H, N.

EXAMPLE 53

N-(4-Chlorophenylsulfonyl)-L-valyl-L-tryptophanal

Valine (13.1 g) was dissolved in 1M aqueous sodium hydroxide solution (100 ml), and purified water (250 ml) and tetrahydrofuran (100 ml) were added. Thereto were alternately added 1M aqueous sodium hydroxide solution (100 ml) and a solution (100 ml) of 4-chlorobenzenesulfonyl chloride (19.0 g) in tetrahydrofuran in 1/5 portions thereof with stirring under ice-cooling. The solution was stirred for one day at room temperature to allow reaction. After the completion of the reaction, the reaction mixture was adjusted to pH 2–3 and extracted with ethyl acetate. The extract was washed with dilute hydrochloric acid and saturated brine, and dried over anhydrous magnesium sulfate. Ethyl acetate was evaporated under reduced pressure, and the residue was washed with a mixture of hexane-ethyl acetate to give 13.6 g of N-(4-chlorophenylsulfonyl)-L-valine as white crystals.

N-(4-Chlorophenylsulfonyl)-L-valine (13.5 g) and N-hydroxysuccinimide (6.4 g) were dissolved in tetrahydrofuran (200 ml), and a solution (200 ml) of 1-ethyl-3-(3-dimethylaminopropyl)carbodiimide hydrochloride (10.6 g) in dichloromethane was gradually added dropwise with stirring under ice-cooling. The solution was stirred at room temperature for about 12 hr to allow reaction. After the completion of the reaction, the solvent was evaporated under reduced pressure and the residue was dissolved in ethyl acetate. The mixture was washed with dilute hydrochloric acid, saturated aqueous solution of sodium hydrogencarbonate and saturated brine, and dried over anhydrous magnesium sulfate. Ethyl acetate was evaporated under reduced pressure, and the residue was washed with a mixed solution of hexane-ethyl acetate to give 14.3 g of N-(4-chlorophenylsulfonyl)-L-valine N-hydroxysuccinimide ester as white crystals.

N-(4-Chlorophenylsulfonyl)-L-valine N-hydroxysuccinimide ester (1.5 g) and L-tryptophanol (0.88 g) were added to dichloromethane (100 ml), and the mixture was stirred at room temperature while adding triethylamine (1.2 g). The solution was stirred for 2 hr to allow reaction. After the completion of the reaction, the solvent was evaporated under reduced pressure. The residue was dissolved in ethyl acetate, washed with dilute hydrochloric acid, saturated aqueous solution of sodium hydrogencarbonate and saturated brine, and dried over anhydrous magnesium sulfate. Ethyl acetate was evaporated under reduced pressure, and the residue was washed with a mixed solution of hexane-ethyl acetate to give 1.6 g of N-(4-chlorophenylsulfonyl)-L-valyl-L-triptophanol as white crystals.

N-(4-Chlorophenylsulfonyl)-L-valyl-L-tryptophanol (1.5 g) was dissolved in dimethyl sulfoxide (20 ml) and dichloromethane (15 ml), and triethylamine (2.0 g) was added. The solution was stirred at room temperature while adding a solution (20 ml) of sulfur trioxide-pyridine complex (2.1 g) in dimethyl sulfoxide, which was followed by stirring for 1 hr. After the completion of the reaction, ethyl acetate was added. The mixture was washed with dilute hydrochloric acid, saturated aqueous solution of sodium hydrogencarbonate and saturated brine, and dried over anhydrous magnesium sulfate. The solvent was evaporated under reduced pressure, and the residue was purified by preparative TLC plate (developing solvent: hexane-ethyl acetate, 1:1, v/v) to give 0.10 g of N-(4-chlorophenylsulfonyl)-L-valyl-L-tryptophanal (Compound 48) as white crystals. [Step 1]

$^1$H-NMR (DMSO-$d_6$ 270 MHz) δ: 0.81 (d, 3H, J=6.8 Hz), 0.82 (d, 3H, J=6.4 Hz), 1.77–1.91(m, 1H), 2.82 (dd, 1H, J=7.8, 15.1 Hz), 3.07 (dd, 1H, J=5.9, 15.1 Hz), 3.65 (dd, 1H, J=6.8, 9.3 Hz), 4.06–4.14 (m, 1H), 6.96–7.69 (m, 9H), 7.99 (d, 1H, J=9.8 Hz), 8.41 (d, 1H, J=6.4 Hz), 9.21 (s, 1H), 10.92 (s, 1H).

Anal. ($C_{22}H_{24}ClN_3O_4S$) C, H, N.

In the same manner as in Step 1 except that 4-fluorobenzenesulfonyl chloride was used instead of 4-chlorobenzenesulfonyl chloride of Step 1, N-(4-fluorophenylsulfonyl)-L-valyl-L-tryptophanal (Compound 49) was obtained as white crystals. [Step 2]

$^1$H-NMR (DMSO-$d_6$ 270 MHz) δ: 0.80 (d, 3H, J=6.8 Hz), 0.81 (d, 3H, J=6.8 Hz), 1.76–1.88 (m, 1H), 2.82 (dd, 1H, J=8.1, 15.1 Hz), 3.06 (dd, 1H, J=6.1, 15.1 Hz), 3.63 (dd, 1H, J=6.8, 9.3 Hz) 4.04–4.12 (m, 1H), 6.98–7.56 (m, 7H), 7.68–7.76 (m, 2H), 7.93 (d, 1H, J=9.3 Hz), 8.41 (d, 1H, J=6.4 Hz), 9.19 (s, 1H), 10.92 (s, 1H).

Anal. ($C_{22}H_{24}FN_3O_4S$) C, H, N.

In the same manner as in Step 1 except that 2-naphthalenesulfonyl chloride was used instead of 4-chlorobenzenesulfonyl chloride, and 1-aminocyclohexanecarboxylic acid was used instead of valine of Step 1, 1-(2-naphthalenesulfonylamino)cyclohexanecarbonyl-L-tryptophanal (Compound 50) was obtained as white crystals. [Step 3]

$^1$H-NMR (DMSO-$d_6$ 270 MHz) δ: 1.17 (s br, 6H), 1.72 (s br, 4H), 2.97–3.16 (m, 2H), 4.10–4.17 (m, 1H), 6.95–7.22 (m, 3H), 7.33 (d, 1H, J=8.3 Hz), 7.48 (d, 1H, J=7.6 Hz), 7.61–7.72 (m, 2H), 7.83–8.14 (m, 6H), 8.41 (s, 1H), 10.89 (s, 1H).

Anal. ($C_{28}H_{29}N_3O_4S$) C, H, N.

In the same manner as in Step 1 except that 2-naphthalenesulfonyl chloride was used instead of 4-chlorobenzenesulfonyl chloride, and tert-leucine was used instead of valine of Step 1, N-(2-naphthalenesulfonyl)-L-tert-leucyl-L-tryptophanal (Compound 51) was obtained as white crystals.

$^1$H-NMR (DMSO-$d_6$ 270 MHz) δ: 0.89 (s, 9H), 2.43 (dd, 1H, J=6.8, 15.1 Hz), 2.68 (dd, 1H, J=7.3, 15.1 Hz), 3.64–3.75 (m, 2H), 6.93–7.16 (m, 3H), 7.19 (d, 1H, J=7.8 Hz), 7.32 (d, 1H, J=8.3 Hz), 7.58–7.67 (m, 2H), 7.76–7.80 (m, 2H), 7.88–8.01 (m, 3H), 8.05–8.09 (m, 1H), 8.37 (d, 1H, J=6.4 Hz), 8.43 (m, 1H), 8.83 (s, 1H), 10.80 (s, 1H).

Anal. ($C_{27}H_{29}N_3O_4S$) C, H, N.

EXAMPLE 54

N-(4-Fluorophenylsulfonyl)-L-valyl-L-cyclohexylalaninal

Valine (11.5 g) was dissolved in 1M aqueous sodium hydroxide solution (100 ml), and purified water (200 ml) and tetrahydrofuran (100 ml) were added. Thereto were simultaneously added dropwise 1M aqueous sodium hydroxide solution (100 ml) and a solution (100 ml) of 4-fluorobenzenesulfonyl chloride (17.5 g) in tetrahydrofuran with stirring under ice-cooling. The solution was stirred for one day at room temperature to allow reaction. After the completion of the reaction, the reaction mixture was adjusted to pH 2–3 and extracted with ethyl acetate. The extract was washed with dilute hydrochloric acid and saturated brine, and dried over anhydrous magnesium sulfate. Ethyl acetate was evaporated under reduced pressure, and the residue was washed with a mixture of hexane-ethyl acetate to give 15.5 g of N-(4-fluorophenylsulfonyl)-L-valine as white crystals.

N-(4-Fluorophenylsulfonyl)-L-valine (12.0 g) and N-hydroxysuccinimide (7.6 g) were dissolved in tetrahydrofuran (200 ml), and a solution (200 ml) of 1-ethyl-3-(3-dimethylaminopropyl)carbodiimide hydrochloride (12.6 g) in dichloromethane was gradually added dropwise with stirring under ice-cooling. The solution was stirred at room temperature for about 4 hr to allow reaction. After the completion of the reaction, the solvent was evaporated under reduced pressure and the residue was dissolved in ethyl acetate. The mixture was washed with dilute hydrochloric acid, saturated aqueous solution of sodium hydrogencarbonate and saturated brine, and dried over anhydrous magnesium sulfate. Ethyl acetate was evaporated under reduced pressure, and the residue was washed with a mixed solution of hexane-ethyl acetate to give 14.1 g of N-(4-fluorophenylsulfonyl)-L-valine N-hydroxysuccinimide ester as white crystals.

N-(4-Fluorophenylsulfonyl)-L-valine N-hydroxysuccinimide ester (1.5 g) and (S)-2-amino-3-cyclohexyl-1-propanol hydrochloride (1.5 g) were added to dichloromethane (80 ml), and the mixture was stirred at room temperature while adding triethylamine (2.0 g). The solution was stirred for 2 hr to allow reaction. After the completion of the reaction, the solvent was evaporated under reduced pressure. The residue was dissolved in ethyl acetate, washed with dilute hydrochloric acid, saturated aqueous solution of sodium hydrogencarbonate and saturated brine, and dried over anhydrous magnesium sulfate. Ethyl acetate was evaporated under reduced pressure, and the residue was washed with a mixed solution of hexane-ethyl acetate to give 1.4 g of N-(4-fluorophenylsulfonyl)-L-valyl-L-cyclohexylalaninol as white crystals.

N-(4-Fluorophenylsulfonyl)-L-valyl-L-cyclohexylalaninol (1.3 g) was dissolved in dimethyl sulfoxide (20 ml) and dichloromethane (10 ml), and triethylamine (1.9 g) was added. The solution was stirred at room temperature while adding a solution (10 ml) of sulfur trioxide-pyridine complex (2.0 g) in dimethyl sulfoxide, which was followed by stirring for 1 hr. After the completion of the reaction, ethyl acetate was added. The mixture was washed with dilute hydrochloric acid, saturated aqueous solution of sodium hydrogencarbonate and saturated brine, and dried over anhydrous magnesium sulfate. The solvent was evaporated under reduced pressure, and the residue was purified by preparative TLC plate (developing solvent: hexane-ethyl acetate, 1:1, v/v) to give 0.37 g of N-(4-fluorophenylsulfonyl)-L-valyl-L-cyclohexylalaninal (Compound 52) as white crystals. [Step 1]

$^1$H-NMR (DMSO-d$_6$ 270 MHz) δ: 0.74–1.61 (m, 13H), 0.82 (d, 3H, J=10.9 Hz), 0.84 (d, 3H, J=10.9 Hz), 1.80–1.93 (m, 1H), 3.53–3.66 (m, 1H), 3.77–3.85 (m, 1H), 7.32–7.42 (m, 2H), 7.79–7.87 (m, 2H), 7.96 (d, 1H, J=8.9 Hz), 8.29 (d, 1H, J=6.6 Hz), 9.10 (s, 1H).

Anal. ($C_{20}H_{29}FN_2O_4S$) C, H, N.

In the same manner as in Step 1 except that 2-naphthalenesulfonyl chloride was used instead of 4-fluorobenzenesulfonyl chloride, N-(2-naphthalenesulfonyl)-L-valyl-L-cyclohexylalaninal (Compound 53) was obtained as white crystals.

$^1$H-NMR (DMSO-d$_6$ 270 MHz) δ: 0.52–0.82 (m, 13H), 0.82 (d, 3H, J=6.6 Hz), 0.84 (d, 3H, J=5.6 Hz), 1.81–1.99 (m, 1H), 3.63–3.69 (m, 2H), 7.80 (dd, 1H, J=1.9, 8.8 Hz), 8.00–8.11 (m, 4H), 8.26 (d, 1H, J=6.6 Hz), 8.39 (m, 1H), 8.96 (s, 1H).

Anal. ($C_{24}H_{32}N_2O_4S$) C, H, N.

In the same manner as in Step 1 except that 4-chlorophenylsulfonyl chloride was used instead of 4-fluorobenzenesulfonyl chloride, N-(4-chlorophenylsulfonyl)-L-valyl-L-cyclohexylalaninal (Compound 54) was obtained as white crystals.

$^1$H-NMR (DMSO-d$_6$ 270 MHz) δ: 0.74–1.61 (m, 13H), 0.82 (d, 3H, J=10.2 Hz), 0.85 (d, 3H, J=10.5 Hz), 1.89–1.93 (m, 1H), 3.58–3.63 (m, 1H), 3.77–3.85 (m, 1H), 7.58–7.63 (m, 2H), 7.75–7.80 (m, 2H), 8.05 (d, 1H, J=7.3 Hz), 8.40 (d, 1H, J=6.6 Hz), 9.11 (s, 1H).

Anal. ($C_{20}H_{29}Cl$-$N_2O_4S$) C, H, N.

EXAMPLE 55

N-(4-Fluorophenylsulfonyl)-D-valyl-D-leucinal

D-Valine (6.6 g) was dissolved in 1M aqueous sodium hydroxide solution (50 ml), and purified water (200 ml) and tetrahydrofuran (100 ml) were added. Thereto were simultaneously added dropwise 1M aqueous sodium hydroxide solution (100 ml) and a solution (50 ml) of 4-fluorobenzenesulfonyl chloride (9.7 g) in tetrahydrofuran with stirring under ice-cooling. The solution was stirred for one day at room temperature to allow reaction. After the completion of the reaction, the reaction mixture was adjusted to pH 2–3 and extracted with ethyl acetate. The extract was washed with dilute hydrochloric acid and saturated brine, and dried over anhydrous magnesium sulfate. Ethyl acetate was evaporated under reduced pressure, and the residue was washed with a mixture of hexane-ethyl acetate to give 8.3 g of N-(4-fluorophenylsulfonyl)-L-valine as white crystals.

N-(4-Fluorophenylsulfonyl)-L-valine (8.0 g) and N-hydroxysuccinimide (4.4 g) were dissolved in tetrahydrofuran (150 ml), and a solution (150 ml) of 1-ethyl-3-(3-dimethylaminopropyl)carbodiimide hydrochloride (7.3 g) in dichloromethane was gradually added with stirring under ice-cooling. The solution was stirred at room temperature for about 12 hr to allow reaction. After the completion of the reaction, the solvent was evaporated under reduced pressure and the residue was dissolved in ethyl acetate. The mixture was washed with dilute hydrochloric acid, saturated aqueous solution of sodium hydrogencarbonate and saturated brine, and dried over anhydrous magnesium sulfate. Ethyl acetate was evaporated under reduced pressure, and the residue was washed with a mixed solution of hexane-ethyl acetate to give 9.6 g of N-(4-fluorophenylsulfonyl)-D-valine N-hydroxysuccinimide ester as white crystals.

N-(4-Fluorophenylsulfonyl)-D-valine N-hydroxysuccinimide ester (1.8 g) and D-leucinol (0.74 g) were added to dichloromethane (80 ml), and the mixture was stirred at room temperature while adding triethylamine (1.5 g). The solution was stirred for 2 hr to allow reaction. After the completion of the reaction, the solvent was evaporated under reduced pressure. The residue was dissolved in ethyl acetate, washed with dilute hydrochloric acid, saturated aqueous solution of sodium hydrogencarbonate and saturated brine, and dried over anhydrous magnesium sulfate. Ethyl acetate was evaporated under reduced pressure, and the residue was washed with a mixed solution of hexane-ethyl acetate to give 1.6 g of N-(4-fluorophenylsulfonyl)-D-valyl-D-leucinol as white crystals.

N-(4-Fluorophenylsulfonyl)-D-valyl-D-leucinol (1.5 g) was dissolved in dimethyl sulfoxide (20 ml) and dichloromethane (10 ml), and triethylamine (2.4 g) was added. The solution was stirred at room temperature while adding a solution (20 ml) of sulfur trioxide-pyridine complex (2.6 g) in dimethyl sulfoxide, which was followed by stirring for 1 hr. After the completion of the reaction, ethyl acetate was added. The mixture was washed with dilute hydrochloric acid, saturated aqueous solution of sodium hydrogencarbonate and saturated brine, and dried over anhydrous magnesium sulfate. The solvent was evaporated under reduced pressure, and the residue was purified by preparative TLC plate (developing solvent: hexane-ethyl acetate, 1:1, v/v) to give 1.0 g of N-(4-fluorophenylsulfonyl)-D-valyl-D-leucinal (Compound 55) as white crystals. [Step 1]

$^1$H-NMR (DMSO-d$_6$ 270 MHz) δ: 0.74 (d, 3H, J=6.3 Hz), 0.82 (d, 6H, J=6.3 Hz), 0.87 (d, 3H, J=6.9 Hz), 1.15–1.45 (m, 3H), 1.81–1.93 (m, 1H), 3.59 (t, 1H, J=6.8 Hz), 3.80–3.88 (m, 1H), 7.33–7.42 (m, 2H), 7.79–7.86 (m, 2H), 7.95 (d, 1H, J=6.9 Hz), 8.26 (d, 1H, J=6.9 Hz), 9.14 (s, 1H).

Anal. ($C_{22}H_{30}N_2O_4S$) C, H, N.

In the same manner as in Step 1 except that valine was used instead of D-valine, N-(4-fluorophenylsulfonyl)-L-valyl-D-leucinal (Compound 56) was obtained as white crystals. [Step 2]

$^1$H-NMR (DMSO-d$_6$ 270 MHz) δ: 0.78 (d, 3H, J=6.3 Hz), 0.82 (d, 3H, J=6.6 Hz), 0.83 (d, 6H, J=6.3 Hz), 1.18–1.50 (m, 3H), 1.79–1.92 (m, 1H), 3.61–3.63 (m, 1H), 3.84–3.92 (m, 1H), 7.33–7.44 (m, 2H), 7.80–7.96 (m, 3H), 8.22 (d, 1H, J=6.9 Hz), 8.96 (s, 1H).

Anal. ($C_{20}H_{29}FN_2O_4S$) C, H, N.

EXAMPLE 56

| (Tablet) | |
|---|---|
| Compound 35 | 30 mg |
| Lactose | 80 mg |
| Starch | 17 mg |
| Magnesium stearate | 3 mg |

Using the above ingredient as the material for one tablet, tablets are prepared by a conventional method. Where necessary, sugar coating may be applied.

EXAMPLE 57

| (Injection) | |
|---|---|
| Compound 48 | 2.5 mg |
| Sodium chloride | 900 mg |
| 1N sodium hydroxide | q.s. |
| Distilled water for injection | total 100 ml |

The above ingredients are admixed by a conventional method to give injections.

EXAMPLE 58

| (Eye drop) | |
|---|---|
| Compound 35 | 50 mg |
| Boric acid | 700 mg |
| Sodium tetraborate | q.s. |
| Sodium chloride | 500 mg |
| Hydroxymethylcellulose | 500 mg |
| Disodium edetate | 0.05 mg |
| Benzalkonium chloride | 0.005 mg |
| Sterile purified water | total 100 ml |

The above ingredients are admixed by a conventional method to give a suspension for eye drop.

Experimental Example 1

Effect of Cysteine Protease Inhibitor on Angiogenesis in Cornea of Guinea Pig by Transplantation of Basic FGF (bFGF)

(Test Method)

(1) Method for Preparing Pellets for Transplantation

A solution (5 μl) of 8% ethylene vinyl acetate copolymer (EVA) in dichloromethane was dropped on a plate made of Tefron, air-dried, and 0.0167 w/v % bFGF (3 μl) was dropped thereon and air-dried. After drying, the obtained product was rounded into a small rod to give a bFGF (500 ng)-containing pellet.

Using a test solution instead of 0.0167 w/v % bFGF, a test solution-containing pellet was prepared in the same manner as above. The test solution-containing pellets were prepared to contain 27 mer calpastatin peptide (0.03 μmole and 0.1 μmule/pellet, Sigma) and leupeptin (0.1 μmole/pellet, PEPTIDE INSTITUTE, INC.).

As a control, a pellet made of EVA alone was prepared and used as a vehicle pellet.

(2) Transplantation of Pellet into Cornea of Guinea Pig

The procedure followed the method of M. Kusaka et al. [Biochem. Biophys. Res. Comm., vol. 174, pp. 1070–1076 (1991)]. That is, male guinea pigs weighing 300–400 g were anesthetized with a 1:1 mixture of Ketalar 50 (ketamin hydrochloride, Sankyo Company, Limited) and Celactal (xylazine hydrochloride, Bayer, Ltd.). A pocket was formed in the intercellular layer of corneal stroma layer of both eyes from corneal limbus to the center of cornea, using a 0.5 mm width ophthalmic spatula. A test solution-containing pellet was inserted into the pocked thus formed, and a bFGF-containing pellet was inserted in adjacency thereto. For prevention of infection, ofloxacin eye ointment [Tarivid eye ointment (ofloxacin 0.3%, manufactured by Santen Pharmaceutical Co., Ltd.) was instilled once immediately after insertion of the pellets. Thereafter, 0.3% lomefloxacin (lomeflon ophthalmic otologic solution, manufactured by Senju Pharmaceutical Co., Ltd.) was instilled once a day for 5 days.

(3) Evaluation of the Effects of Cysteine Protease Inhibitor

The effect of the cysteine protease inhibitor was observed with a slit lamp. The blood vessel newly formed in cornea which is an avascular tissue had high permeability, and the wet weight and plasma content were expected to elevate due to incurrent of plasma components as a result of high permeability. At 9 days posttransplantation of pellet, guinea pigs were euthanized and cornea was collected. The obtained cornea was weighed (wet weight). Then, it was homogenized, and subjected to centrifugation. The obtained water soluble protein was separated by SDS polyacrylamide gel electrophoresis. After electrophoresis, the gel was stained with Coomassie Brilliant Blue. By image analysis (NIH Image 1.31), albumin which is one of the major proteins in plasma was quantitatively assayed. As the standard substance, guinea pig serum albumin was used.

(Test Results)

(1) Observation of Cornea with a Slit Lamp

Figure 2:
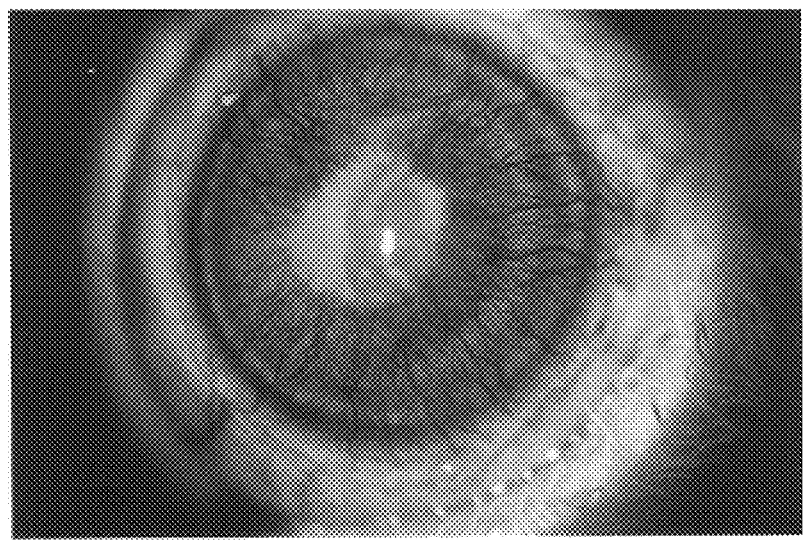
FIG. 2(A) and FIG. 2(B) show cornea of guinea pig observed with a slit lamp, at 9 days after implantation of bFGF-containing pellet, and leupeptin (0.1 μmole)-containing pellet together with bFGF-containing pellet.
Figure 2:
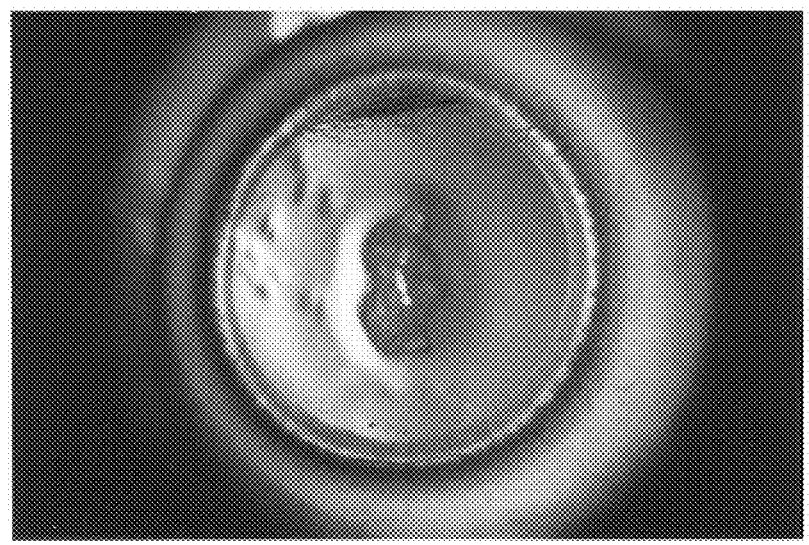

The cornea of vehicle pellet transplantation group showed no changes as compared to the cornea of the untreated group. The bFGF-containing pellet transplantation group (hereinafter sometimes referred to as control group) showed appearance of blood vessel in the neighborhood of bFGF-containing pellet transplantation site from 4 days after transplantation. At 9 days posttransplantation, blood vessels were newly formed radially in the entirety of the cornea of guinea pigs. The group which underwent transplantation of 27 mer calpastatin peptide-containing pellet or leupeptin-containing pellet together with bFGF-containing pellet showed appearance of blood vessel in all groups. Compared to the control group, however, the degree of appearance was mild, and new formation of blood vessels was found mainly in corneal limbus. The corneas at 9 days posttransplantation of guinea pig are shown in FIGS. 1 and 2.

(2) Wet Weight of Cornea

Figure 3:
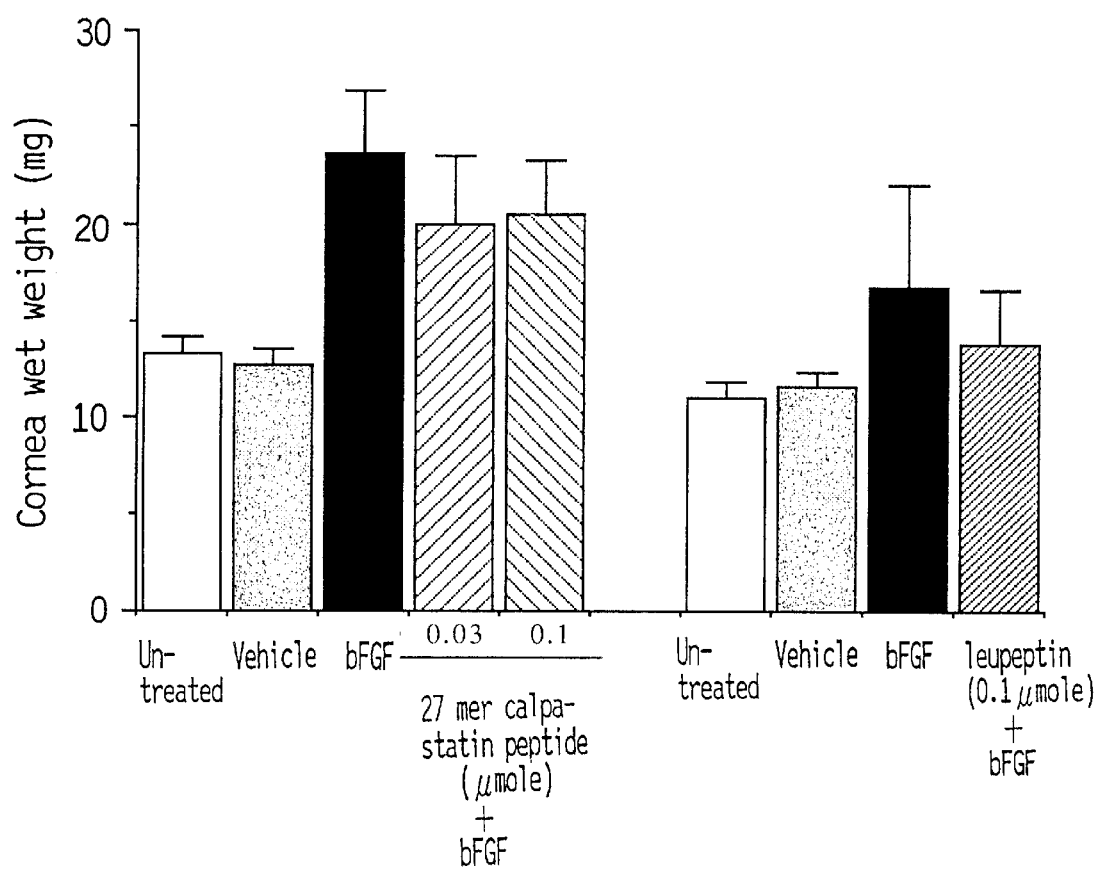
FIG. 3 is a graph showing the wet weight of cornea of guinea pig obtained at 9 days after implantation of bFGF-containing pellet, and 27 mer calpastatin peptide (0.03 μmole and 0.1 μmole)-containing pellet or leupeptin (0.1 μmole)-containing pellet together with bFGF-containing pellet.

The results are shown in FIG. 3. The wet weight of cornea was almost the same between the untreated group and vehicle pellet transplantation group, and no influence by transplantation of vehicle pellet was found. In contrast, the wet weight of cornea of the control group increased from the weight of the untreated group and vehicle pellet transplantation group. The group which underwent transplantation of 27 mer calpastatin peptide-containing pellet or leupeptin-containing pellet together with bFGF-containing pellet showed suppressed increase in the wet weight of cornea as compared to the control group.

It was clarified therefrom that 27 mer calpastatin peptide and leupeptin suppress increase in wet weight of cornea caused by angiogenesis.

(3) Amount of Albumin in Cornea

Figure 4:
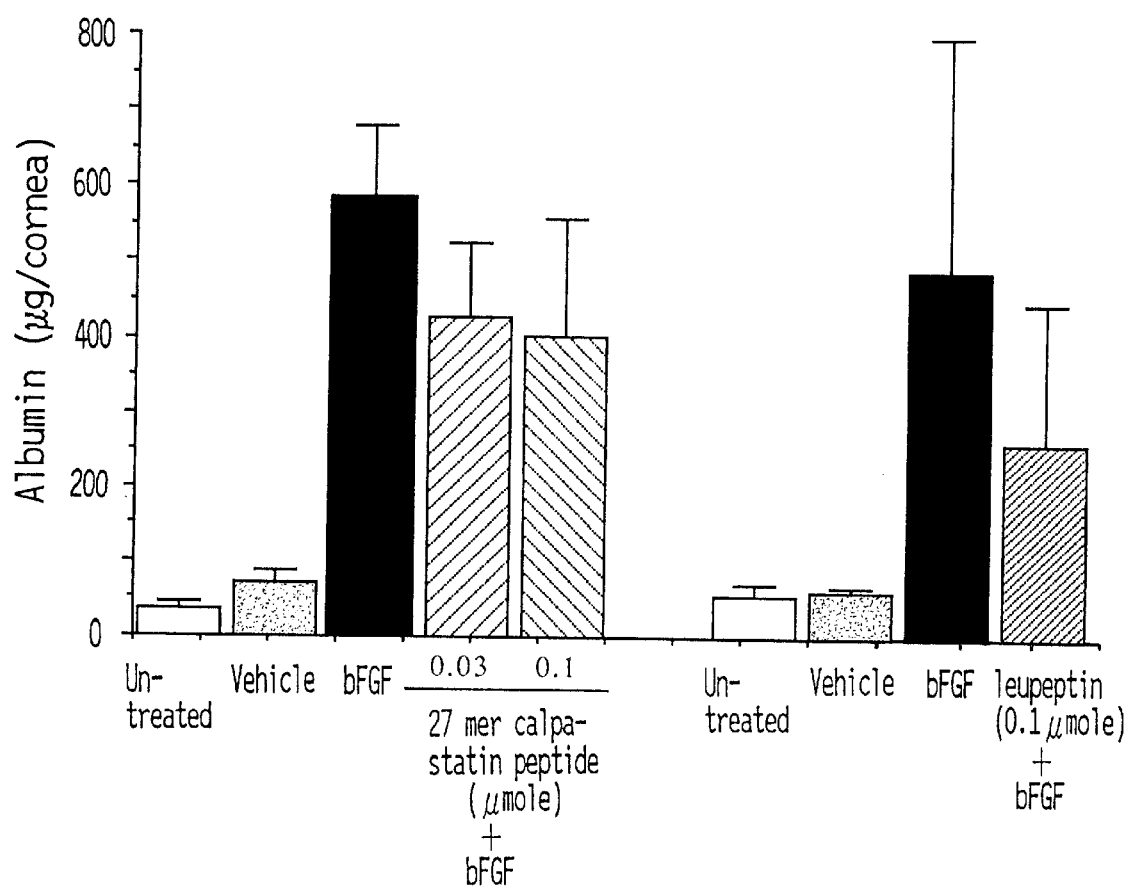
FIG. 4 is a graph showing an amount of albumin in cornea of guinea pig obtained at 9 days after implantation of bFGF-containing pellet, and 27 mer calpastatin peptide (0.03 μmole and 0.1 μmole)-containing pellet or leupeptin (0.1 μmole)-containing pellet together with bFGF-containing pellet.

The results are shown in FIG. 4. The amount of albumin of untreated group was very small and was 35.2±9.6 (S.D.)

or 56.1±13.5 (S.D.). This was because cornea is an avascular tissue. Meanwhile, that of the group which underwent transplantation of vehicle pellet showed a small increase from the weight of the untreated group. This was supposedly attributable to surgical stimulation during pellet transplantation. In contrast, that of the control group was about 17 or 9 times greater than the untreated group, and about 8 times greater than the vehicle pellet transplantation group. This was because vascular permeability was high in newly formed blood vessels, and albumin which is the main component of plasma leaked. The group transplanted with 27 mer calpastatin peptide-containing pellet and leupeptin-containing pellet together with bFGF-containing pellet showed suppressed increase in the amount of albumin in cornea as compared to the control group.

It was clarified from the above that a cysteine protease inhibitor suppressed angiogenesis.

Experimental Example 2

The biological activity of the compounds of the formula (I) and (IV) is shown in the following. The compounds of the formula (I) and (IV) and salts thereof show thiol protease-inhibitory activity. The inhibitory activity against calpain, cathepsin L, papain, and trypsin which is a serine protease was determined. The results are shown in Tables 6 and 7.

$\mu$-Calpain-inhibitory Activity

The activity of $\mu$-calpain (Nakalai Tesque) was assayed in accordance with the procedure described in the literature [Anal. Biochem., 208, 387–392 (1993)]. Thus, to a solution containing 0.5 mg/ml casein, 50 mM Tris-HCl (pH 7.4), 20 mM dithiothreitol, and 4 mM calcium chloride was added 2.5 $\mu$l of a dimethyl sulfoxide solution containing a varying concentration of the test drug as well as 0.03 unit of $\mu$calpain to initiate the reaction. The final liquid volume was 250 $\mu$l. After 60 minutes of reaction at 30° C., 100 $\mu$l of the reaction mixture was transferred to another vessel, to which 50 $\mu$l of purified water and 100 $\mu$l of 50% Coumassie brilliant blue solution were added. The mixture was allowed to stand at room temperature for 15 minutes and the absorbance was measured at 595 nm. As a control, 2.5 $\mu$l of dimethyl sulfoxide not containing the test drug was added and the mixture was treated in the same manner as above. The absorbance value thus found was used as the control value. Similarly, the value found by adding 0.2 mM EDTA in lieu of 4 mM aqueous calcium chloride solution was used as the blank value. The inhibition rate was calculated by means of the following equation and plotted against concentration on log paper and the amount necessary for 50% inhibition ($IC_{50}$) was determined.

$$\text{Inhibition rate (\%)} = \left(1 - \frac{\text{Measured value} - \text{blank value}}{\text{Control value} - \text{blank value}}\right) \times 100$$

Assay of Cathepsin L-inhibitory Activity

The activity of cathepsin L (Cosmo Bio), a cysteine protease, was assayed by the method described in the literature [Methods in Enzymology, 80, 535–561, 1981]. Thus, to a solution containing 85 mM acetate buffer (pH 5.5), 2 mM dithiothreitol, 1 mM EDTA, 2 $\mu$g cathepsin L, and a varying concentration of the test compound was added 50 $\mu$l of 20 $\mu$M carbobenzoxy-L-phenylalanyl-L-arginine-4-methylcoumaryl-7-amide (Z-Phe-Arg-MCA) to initiate the reaction at the final liquid volume of 200 $\mu$l. After 20 minutes of reaction at 30° C., 20 $\mu$l of 1 M Tris-HCl (pH 8.0) was added so as to stop the reaction. The amount of liberated 4-methyl-7-aminocoumarin was determined with a fluorospectrometer at an excitation wavelength of 360 nm and a fluorescent emission wave length of 450 nm. Using the value found without addition of the test drug as control and the value found without addition of the enzyme as blank, $IC_{50}$ was determined in the same manner as above.

Assay of Papain- and Trypsin-inhibitory Activity

The activity of papain which is a cysteine protease and of trypsin (Sigma) which is a serine protease was assayed in accordance with the method described in the literature [Anal. Biochem., 208, 387–392, 1993]. Thus, to a solution containing 0.5 mg/ml casein, 50 mM Tris-HCl (pH 8.0), 20 mM dithiothreitol, and 0.2 mM EDTA was added 2.5 $\mu$l of dimethyl sulfoxide containing a varying concentration of the test drug as well as 0.03 unit of papain or trypsin to initiate the reaction. The final liquid volume was adjusted to 250 $\mu$l. After 60 minutes of reaction at 30° C., 100 $\mu$l of the reaction mixture was transferred to another vessel and following addition of 50 $\mu$l of purified water and 100 $\mu$l of 50% Coumassie brilliant blue solution, the mixture was allowed to stand at room temperature for 15 minutes. The absorbance of the mixture was then measured at 595 nm. Using the value found similarly by adding 2.5 $\mu$l of dimethyl sulfoxide not containing the test drug as control and the value found without addition of the enzyme as blank, IC50 was determined in the same manner as above.

TABLE 6

Calpain 50% inhibitory concentration ($IC_{50}$)

| Test drug | (M) |
| --- | --- |
| Compound 3 | $4.7 \times 10^{-5}$ |
| Compound 11 | $2.9 \times 10^{-6}$ |
| Compound 13 | $8.1 \times 10^{-7}$ |
| Compound 14 | $7.8 \times 10^{-7}$ |
| Compound 15 | $1.1 \times 10^{-6}$ |
| Compound 16 | $6.4 \times 10^{-7}$ |
| Compound 17 | $3.5 \times 10^{-7}$ |
| Compound 18 | $6.3 \times 10^{-7}$ |
| Compound 19 | $4.9 \times 10^{-7}$ |
| Compound 20 | $1.2 \times 10^{-6}$ |
| Compound 21 | $9.5 \times 10^{-7}$ |
| Compound 22 | $1.8 \times 10^{-5}$ |
| Compound 23 | $5.1 \times 10^{-6}$ |
| Compound 24 | $8.4 \times 10^{-7}$ |
| Compound 25 | $4.1 \times 10^{-5}$ |
| Compound 27 | $2.4 \times 10^{-3}$ |
| Compound 28 | $3.9 \times 10^{-6}$ |
| Compound 29 | $6.0 \times 10^{-7}$ |
| Compound 30 | $6.0 \times 10^{-6}$ |
| Compound 31 | $1.5 \times 10^{-4}$ |
| Compound 33 | $1.9 \times 10^{-6}$ |
| Compound 34 | $1.0 \times 10^{-8}$ |
| Compound 35 | $7.5 \times 10^{-9}$ |
| Compound 36 | $3.1 \times 10^{-8}$ |
| Compound 37 | $2.8 \times 10^{-8}$ |
| Compound 38 | $6.1 \times 10^{-6}$ |
| Compound 39 | $4.2 \times 10^{-6}$ |
| Compound 40 | $2.6 \times 10^{-7}$ |
| Compound 41 | $1.3 \times 10^{-7}$ |
| Compound 42 | $3.2 \times 10^{-6}$ |
| Compound 43 | $2.7 \times 10^{-8}$ |
| Compound 44 | $1.4 \times 10^{-8}$ |
| Compound 45 | $1.4 \times 10^{-8}$ |
| Compound 46 | $1.8 \times 10^{-8}$ |
| Compound 47 | $2.0 \times 10^{-7}$ |
| Compound 48 | $1.3 \times 10^{-8}$ |

TABLE 6-continued

| Calpain 50% inhibitory concentration ($IC_{50}$) | |
|---|---|
| Test drug | (M) |
| Compound 49 | $2.3 \times 10^{-8}$ |
| Compound 50 | $3.6 \times 10^{-7}$ |
| Compound 51 | $1.1 \times 10^{-6}$ |
| Compound 52 | $3.0 \times 10^{-8}$ |
| Compound 53 | $8.3 \times 10^{-9}$ |
| Compound 54 | $1.4 \times 10^{-8}$ |
| Compound 55 | $1.0 \times 10^{-4}$ |
| Compound 56 | $1.4 \times 10^{-6}$ |

TABLE 7

| Test drug (Compound No.) | 50% Inhibitory concentration ($IC_{50}$) | | |
|---|---|---|---|
| | Cathepsin L (M) | Papain (M) | Trypsin (M) |
| Compound 11 | $1.2 \times 10^{-8}$ | $1.1 \times 10^{-7}$ | $>3.0 \times 10^{-3}$ |
| Compound 13 | $2.9 \times 10^{-8}$ | $7.9 \times 10^{-8}$ | $>3.0 \times 10^{-3}$ |
| Compound 16 | $8.2 \times 10^{-8}$ | $2.1 \times 10^{-7}$ | $>3.0 \times 10^{-3}$ |
| Compound 17 | $2.7 \times 10^{-8}$ | $6.2 \times 10^{-8}$ | $>3.0 \times 10^{-3}$ |
| Compound 22 | $3.8 \times 10^{-5}$ | $4.0 \times 10^{-6}$ | $>3.0 \times 10^{-3}$ |
| Compound 24 | $9.0 \times 10^{-9}$ | $4.7 \times 10^{-8}$ | $>3.0 \times 10^{-3}$ |

As is evident from the above experimental results, the cysteine protease inhibitory compound to be used in the present invention showed no toxicity to human and animals.

Having inhibitory activity against cysteine proteases such as calpain, cathepsin L and papain and showing no activity against serine protease (trypsin), the compounds of formulas (I) and (IV) and salts thereof are useful as prophylactic or therapeutic agents for a variety of cysteine protease-associated diseases, such as ischemic diseases, inflammatory diseases, muscular dystrophy, cataract, immune diseases, essential hypertension, Alzheimer's disease, subarachnoid hemorrhage, and osteoporosis, in mammals (e.g. mouse, rat, rabbit, dog, cat, bovine, swine, and human).

The angiogenesis inhibitor of the present invention suppresses new formation of blood vessels in the living tissues, so that it can be used as a superior therapeutic or prophylactic agent of angiogenesis associated with wound healing, inflammation, growth of tumor and the like; and angiogenesis as seen in diabetic retinopathy, prematurity retinopathy, retinal venous occlusion, senile discoid macular degeneration and the like, as well as for prevention of metastasis of tumors.

What is claimed is:
1. The compound N-(4-Fluorophenylsulfonyl)-L-valyl-L-leucinal or a salt thereof.

* * * * *